United States Patent
Blatter et al.

(10) Patent No.: US 6,736,825 B2
(45) Date of Patent: May 18, 2004

(54) PAIRED EXPANDABLE ANASTOMOSIS DEVICES AND RELATED METHODS

(75) Inventors: Duane D. Blatter, Salt Lake City, UT (US); Michael C. Barrus, Bountiful, UT (US); Troy J. Orr, Sandy, UT (US)

(73) Assignee: Integrated Vascular Interventional Technologies, L C (IVIT LC), Salt Lake City, UT (US)

(*) Notice: Subject to any disclaimer, the term of this patent is extended or adjusted under 35 U.S.C. 154(b) by 160 days.

(21) Appl. No.: 10/035,084

(22) Filed: Dec. 27, 2001

(65) Prior Publication Data

US 2002/0058955 A1 May 16, 2002

Related U.S. Application Data

(63) Continuation-in-part of application No. 09/737,200, filed on Dec. 14, 2000, which is a continuation-in-part of application No. 09/460,740, filed on Dec. 14, 1999, now Pat. No. 6,569,173.

(51) Int. Cl.⁷ .............................................. A61B 17/08
(52) U.S. Cl. ...................................................... 606/153
(58) Field of Search ......................................... 606/153

(56) References Cited

U.S. PATENT DOCUMENTS

| | | |
|---|---|---|
| 1,151,300 A | 8/1915 | Soresi |
| 3,254,650 A | 6/1966 | Collito |
| 3,254,651 A | 6/1966 | Collito |
| 3,258,012 A | 6/1966 | Nakayama et al. |
| 3,435,823 A | 4/1969 | Edwards |
| 3,774,615 A | 11/1973 | Lim et al. |
| 4,214,587 A | 7/1980 | Sakura, Jr. |
| 4,233,981 A | 11/1980 | Schomacher |
| 4,294,255 A | 10/1981 | Geroc |
| 4,352,358 A | 10/1982 | Angelchik |
| 4,366,819 A | 1/1983 | Kaster |
| 4,368,736 A | 1/1983 | Kaster |
| 4,523,592 A | 6/1985 | Daniel |
| 4,553,542 A | 11/1985 | Schenck et al. |
| 4,593,693 A | 6/1986 | Schenck |
| 4,598,712 A | 7/1986 | Rebuffat et al. |
| 4,607,637 A | 8/1986 | Berggren et al. |
| 4,624,255 A | 11/1986 | Schenck et al. |
| 4,624,257 A | 11/1986 | Berggren et al. |
| 4,657,019 A | 4/1987 | Walsh et al. |
| 4,667,673 A | 5/1987 | Li |
| 4,721,109 A | 1/1988 | Healey |
| 4,803,984 A | 2/1989 | Narayanan et al. |
| 4,848,367 A | 7/1989 | Avant et al. |
| 4,861,336 A | 8/1989 | Helzel |
| 4,873,977 A | 10/1989 | Avant et al. |
| 4,907,591 A | 3/1990 | Vasconcellos et al. |
| 4,917,087 A | 4/1990 | Walsh et al. |
| 4,917,090 A | 4/1990 | Berggren et al. |
| 4,917,091 A | 4/1990 | Berggren et al. |
| 4,917,114 A | 4/1990 | Green et al. |
| 4,930,674 A | 6/1990 | Barak |
| 4,931,057 A | 6/1990 | Cummings et al. |

(List continued on next page.)

Primary Examiner—Gary Jackson
(74) Attorney, Agent, or Firm—Stoel Rives LLP

(57) ABSTRACT

A paired, expandable anastomosis device joins two vessels together and can expand and contract with changes in the size of the two vessels. The anastomosis device has two expandable rings with a plurality of holding tabs. The holding tabs of one ring are shaped to enable a graft vessel tissue to be everted through one of the rings and to be held on one of the rings. Similarly, the holding tabs of the other ring are shaped to enable a target vessel to be everted through the other ring and to be retained by the holding tabs. Once the graft and target vessels are loaded, the rings are adapted to be brought together to a position in which the graft and target vessels are anastomosed together.

36 Claims, 20 Drawing Sheets

U.S. PATENT DOCUMENTS

| | | |
|---|---|---|
| 5,035,702 A | 7/1991 | Taheri |
| 5,047,039 A | 9/1991 | Avant et al. |
| 5,122,156 A | 6/1992 | Granger et al. |
| 5,234,447 A | 8/1993 | Kaster et al. |
| 5,254,113 A | 10/1993 | Wilk |
| 5,336,233 A | 8/1994 | Chen |
| 5,366,462 A | 11/1994 | Kaster et al. |
| 5,456,712 A | 10/1995 | Maginot |
| 5,456,714 A | 10/1995 | Owen |
| 5,478,320 A | 12/1995 | Trotta |
| 5,478,354 A | 12/1995 | Tovey et al. |
| 5,549,122 A | 8/1996 | Detweilwer |
| 5,634,936 A | 6/1997 | Linden et al. |
| 5,662,700 A | 9/1997 | Lazarus |
| 5,695,504 A | 12/1997 | Gifford, III et al. |
| 5,702,412 A | 12/1997 | Popov et al. |
| 5,707,362 A | 1/1998 | Yoon |
| 5,755,778 A | 5/1998 | Kleshinski |
| 5,817,113 A | 10/1998 | Gifford, III et al. |
| 5,843,088 A | 12/1998 | Barra et al. |
| 5,868,763 A | 2/1999 | Spence et al. |
| 5,868,770 A | 2/1999 | Rygaard |
| 5,893,369 A | 4/1999 | LeMole |
| 5,951,576 A | 9/1999 | Wakabayashi |
| 5,976,178 A | 11/1999 | Goldsteen et al. |
| 6,007,576 A | 12/1999 | McClellan |
| 6,030,392 A | 2/2000 | Dakov |
| 6,036,700 A | 3/2000 | Stefanchik et al. |
| 6,036,703 A | 3/2000 | Evans et al. |
| 6,066,148 A | 5/2000 | Rygaard |
| 6,068,637 A | 5/2000 | Popov et al. |
| 6,113,612 A | 9/2000 | Swanson et al. |
| 6,152,937 A | 11/2000 | Peterson et al. |
| 6,187,020 B1 | 2/2001 | Zegdi et al. |
| 6,190,396 B1 | 2/2001 | Whitin et al. |
| 6,190,397 B1 | 2/2001 | Spence et al. |
| 6,193,734 B1 | 2/2001 | Bolduc et al. |
| 6,206,913 B1 | 3/2001 | Yencho et al. |
| 6,210,365 B1 | 4/2001 | Afzal |
| 6,241,743 B1 | 6/2001 | Levin et al. |
| 6,248,117 B1 | 6/2001 | Blatter |
| 6,254,617 B1 | 7/2001 | Spence et al. |
| 6,293,965 B1 | 9/2001 | Berg et al. |
| 6,309,416 B1 | 10/2001 | Swanson et al. |
| 6,355,050 B1 | 3/2002 | Andreas et al. |
| 6,358,258 B1 | 3/2002 | Arcia et al. |
| 6,387,105 B1 | 5/2002 | Gifford, III et al. |
| 6,428,550 B1 | 8/2002 | Vargas et al. |
| 6,485,496 B1 | 11/2002 | Suyker et al. |
| 6,494,889 B1 | 12/2002 | Fleischman et al. |
| 6,503,259 B2 | 1/2003 | Huxel et al. |
| 2002/0082614 A1 | 6/2002 | Logan et al. |

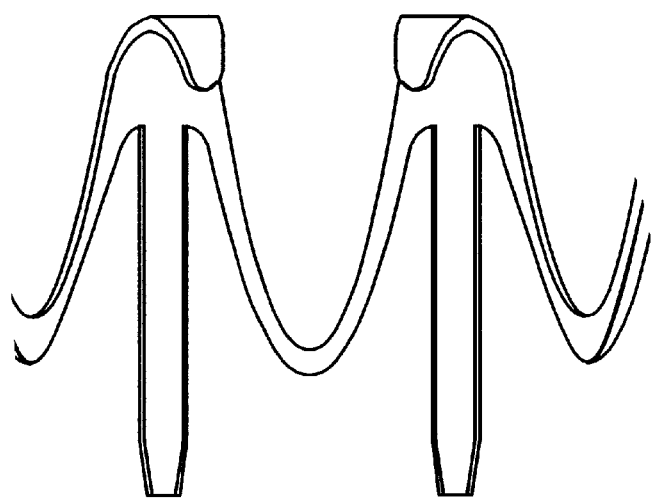
FIG. 5D
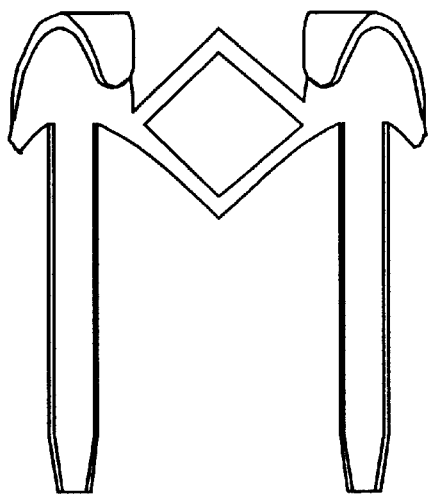
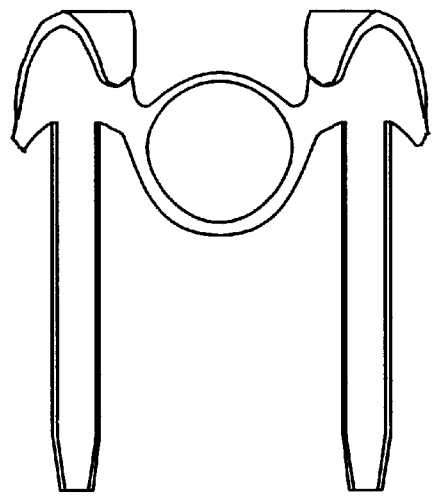
FIG. 5E
FIG. 5F

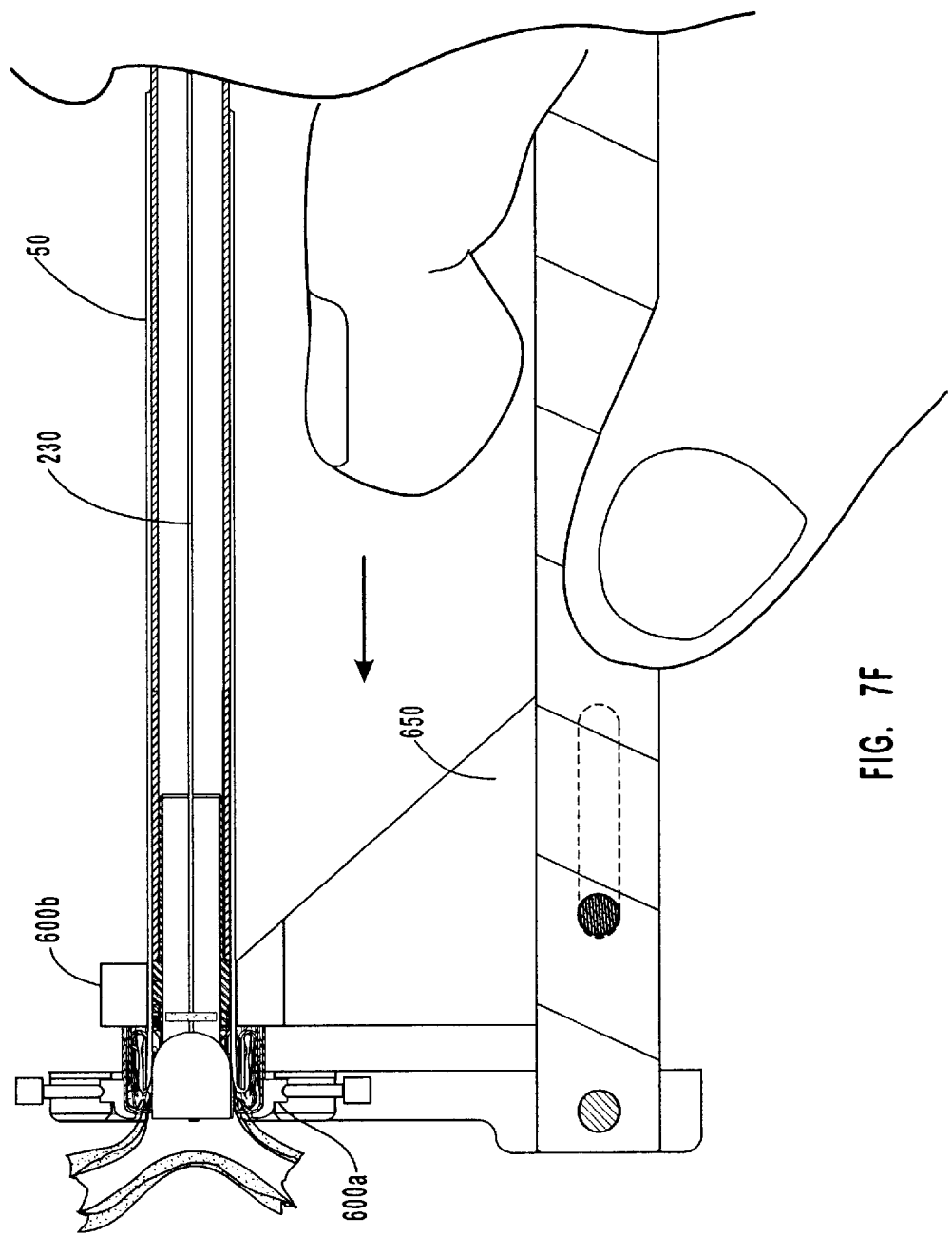

PAIRED EXPANDABLE ANASTOMOSIS DEVICES AND RELATED METHODS

RELATED APPLICATIONS

The present application is a continuation-in-part patent application of U.S. patent application Ser. No. 09/737,200 entitled Compression Plate Anastomosis Apparatus and Related Systems which was filed on Dec. 14, 2000 on behalf of Duane D. Blatter, Kenneth C. Goodrich, Michael C. Barrus, and Bruce M. Burnett. The present application is also a continuation-in-part patent application of U.S. patent application Ser. No. 09/460,740 entitled Ring Anastomosis Apparatus which was filed on Dec. 14, 1999 now U.S. Pat. No. 6,569,173 on behalf of Duane D. Blatter, Kenneth C. Goodrich, Mike Barrus, and Bruce M. Burnett. Ser. No. 09/737,200 is a continuation-in-part patent application of Ser. No. 09/460,740. Ser. No. 09/737,200 and Ser. No. 09/460,740 are both incorporated herein by reference.

TECHNICAL FIELD

The present invention is directed generally to an anastomosis device. More particularly, the present invention is directed a paired, expandable device that joins one vessel to another.

BACKGROUND OF THE INVENTION

An anastomosis is an operative union of two hollow or tubular structures. Anastomotic structures can be part of a variety of systems, such as the vascular system, the digestive system or the genitourinary system. For example, blood is shunted from an artery to a vein in an arteriovenous anastomosis, and from the right pulmonary artery to the superior vena cava in a cavopulmonary anastomosis. In other examples, afferent and efferent loops of jejunum are joined in a Braun's anastomosis after gastroenteroscopy; the ureter and the Fallopian tube are joined in a ureterotubal anastomosis, and the ureter and a segment of the sigmoid colon are joined in a ureterosigmoid anastomosis. In microvascular anastomosis, very small blood vessels are anastomosed usually under surgical microscope.

An anastomosis is termed end-to-end when the terminal portions of tubular structures are anastomosed, and it is termed end-to-side when the terminal portion of a tubular structure is anastomosed to a lateral portion of another tubular or hollow structure. In an end-to-side anastomosis, we often refer to the structure whose end is anastomosed as the "graft vessel" while the structure whose side wall is anastomosed is referred to as the "receiving structure" or "target vessel".

The operative union of two hollow or tubular structures requires that the anastomosis be tight with respect to the flow of matter through such structures and also that the anastomosed structures remain patent for allowing an uninterrupted flow of matter therethrough. For example, anastomosed blood vessels should not leak at the anastomosis site, the anastomotic devices should not significantly disrupt the flow of blood, and the anastomosis itself should not cause a biological reaction that could lead to an obstruction of the anastomosed blood vessels. In particular, anastomosed blood vessels should remain patent and they should ideally not develop hyperplasia, thrombosis, spasms or arteriosclerosis.

Because anastomosed structures are composed of tissues that are susceptible to damage, the anastomosis should furthermore not be significantly detrimental to the integrity of these tissues. For example, injury to endothelial tissue and exposure of subintimal connective tissue should be minimized or even eliminated in vascular anastomosis.

Because structures to be anastomosed are internal, an anastomosis requires a degree of invasion. The invasive character of an anastomosis, however, should be minimized subject to the reliable performance of a satisfactory anastomosis. Accordingly, there has been a noticeable trend during the last quarter of this century towards less invasive surgical intervention, a surgical style that is termed minimally invasive surgery. This style is characterized by pursuing a maximal treatment effect with minimal damage to surrounding and overlying normal structures. In addition, successful minimally invasive procedures should procure patency and they should minimize damage to the tissues of the anastomosed structures themselves.

Particularly in the field of vascular anastomosis, it is acknowledged that there is an increasing demand for an easier, quicker, less damaging, but reliable procedure to create vascular anastomosis. This demand is further revitalized by the movement of vascular procedures towards minimally invasive procedures. See Paul M. N. Werker and Moshe Kon, Review of Facilitated Approaches to Vascular Anastomosis Surgery, Annals of Thoracic Surgery, Vol. 63 (1997) pp. S122–S127.

Anastomosis techniques generally intend to provide leak-proof joints that are not susceptible to mechanical failure, and they also intend to minimize damage and reduce the undesirable effects of certain operational features that may lead to post-anastomosis complications. Damage to be minimized and operational features whose undesirable effects should be reduced include endothelial coverage injury, exposure of subintimal connective tissue, exposure of an intraluminal foreign component, blood flow interruption, irregularities at the junction, adventitial tissue stripping, intimal injury, installment of a foreign rigid body, use of materials that may have toxic effects, damage to surrounding tissue, extensive vessel eversion, and tissue plane malalignment. A common feature of most conventional stapling, coupling and clipping techniques, particularly when applied to small-diameter vessels, is that they require a temporary interruption of the blood stream in the recipient vessel. As the instrumentation that is needed at the anastomosis site becomes complex and cumbersome, a wider open area is needed for accessing the anastomosis site, thus leading to an increasingly invasive procedure.

Post-anastomosis complications include neointimal hyperplasia, atherosclerosis, thrombosis, stenosis, tissue necrosis, vascular wall thinning, and aneurism formation. In particular, potential for thrombosis and for other complications is increased when the anastomosis site does not expand and contract with systole and diastole, causing flow disturbances as blood crosses the anastomosis. Therefore, a flexible and expandable anastomosis device that responds to changing blood pressure during systole and diastole is needed to decrease the potential for thrombosis and other complication.

Potential for flow disturbance at the anastomosis site is also increased when the opening at the anastomosis site has a relatively small diameter. Of course, it is desirable to minimize the size of instruments utilized to form the anastomosis. Smaller instruments minimize the intrusiveness of the procedure. What is needed, therefore, is an anastomosis device that expands upon release and stretches the tissue at the anastomosis opening, enabling the anastomosis to have a larger diameter than the initial anastomosis opening.

Also needed is an anastomosis device that acts external to vessels without penetrating at least one of the vessels and that creates an anastomosis more quickly than conventional techniques, with minimal interruption of blood flow.

SUMMARY OF THE INVENTION

It is an object of the present invention to provide a device for joining vessels together that minimizes complications such as thrombosis through the use of expandable rings that expand and contract with changes in fluid flow through the vessel after anastomosis is complete.

It is a further object of the present invention to provide an anastomosis device that avoids restriction of the lumen at the anastomosis by radially expanding upon deployment, thus minimizing complications such as thrombosis.

Additionally, another object of the invention is to provide an anastomosis device that joins vessels together through the use of expandable rings that are guided to each other by guides.

A further objection of this invention is to provide devices for joining vessels together in a secure manner such that the portions defining the openings of the vessels are not penetrated.

A further object of this invention to provide an anastomosis device that efficiently and reliably joins two vessels together at an anastomosis site.

The present invention is a paired, expandable anastomosis device that joins one vessel opening to another vessel opening. The anastomosis device has two rings. Referred to herein as first and second rings. In one embodiment each ring is made of connected flexible segments. Each flexible segment has two arms that are hingedly connected to form expandable V-shaped segments.

One embodiment of the anastomosis device has a ring is designed so that a portion of a target vessel can be everted through and held on the ring during the anastomosis procedure. The other ring of this embodiment is designed so that a portion of a graft vessel can be everted through and held on the ring during the anastomosis procedure.

Each ring has a holding surface, such as a plurality of holding tabs, to hold the everted vessel tissue. Holding tabs are preferably configured with rounded tips to avoid penetrating the vessel walls. The holding tabs of the ring used to anchor the graft vessel on the ring may have barbs or hooks to more securely hold the graft vessel.

The holding tabs in each ring are preferably oriented relative to the holding tabs of the opposing ring so that when the rings are brought together, each one of the holding tabs in a rings is opposite the space between two neighboring holding tabs in the opposing ring. When the rings are brought together so that the tips of the holding tabs enter or at least close to entering the opposing spaces between the holding tabs of the other ring, the everted tissue will be held together, creating a secure anastomosis.

Once the target and graft vessels are loaded onto the anastomosis device, the rings are guided together. Several embodiments are discussed that enable the rings to be guided together. In one embodiment, the anastomosis device includes a plurality of guides which guide the movement of one ring to the other ring. The rings may have a plurality of guides adapted to receive guideposts. The guides are preferably sized to frictionally engage the guideposts.

The rings have a loading position in which the vessels can be loaded onto the rings. In one embodiment, the guideposts of the second ring are completely inserted into the guides when in the loading position. The guideposts of the first ring are partially inserted into the guides so that the rings maintain an offset configuration. In this loading position, the holding tabs of the first ring are sufficiently spaced from the holding tabs of the second ring so that the graft vessel can be everted onto one ring and the target vessel can be everted onto the other ring. After the rings are loaded, they are brought together to create a secure anastomosis. The rings may be brought together manually or by the use of a device specifically designed for use with the rings, such as an attachment actuaction device. Once the rings are brought together, the frictional engagement of the guides and guideposts prevents the rings from inadvertently sliding on the guides.

The anastomosis device of the present invention provides an efficient, reliable anastomosis. Because the rings are expandable, the inventive anastomosis device minimizes complications caused with anastomosis devices of the prior art. Once the expandable rings are deployed to the anastomosis position, the rings permit the vessel tissue defining the anastomosis to expand and contract with expansion and contraction of the vessels. Additionally, the expandable rings radially expand to a deployed position when released from an external operator or tongs so that the vessel tissues defining the vessel openings are stretched to a diameter greater than the diameter of the initial opening in the target vessel. Also, no foreign material is placed in the interior of the vessel because the vessel tissue is everted onto the rings and the anastomosis is formed by bringing the everted interior of the graft vessel into contact with the everted, interior portion of the target vessel.

BRIEF DESCRIPTION OF THE DRAWINGS

In order that the manner in which the above-recited and other advantages and objects of the invention are obtained, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings in which:

FIGS. 5A–5F depict alternative embodiments of the expandable rings of the present invention.

FIG. 7F is a cross-sectional view of the external anastomosis operator as the attachment actuator device is moved to compress the second compression plate against the first compression plate.

DETAILED DESCRIPTION OF PREFERRED EMBODIMENTS

The present invention relates to a paired expandable anastomosis device adapted to join a first vessel opening in a first vessel to a second vessel opening in a second vessel. The anastomosis device is capable of expanding and contracting in response to changes in fluid pressure in the vessels that are joined together. The anastomosis device is also adapted to radially expand upon deployment, stretching the vessel tissue to create an anastomosis larger than the initial openings in the anastomosed vessels.

Figure 1A:
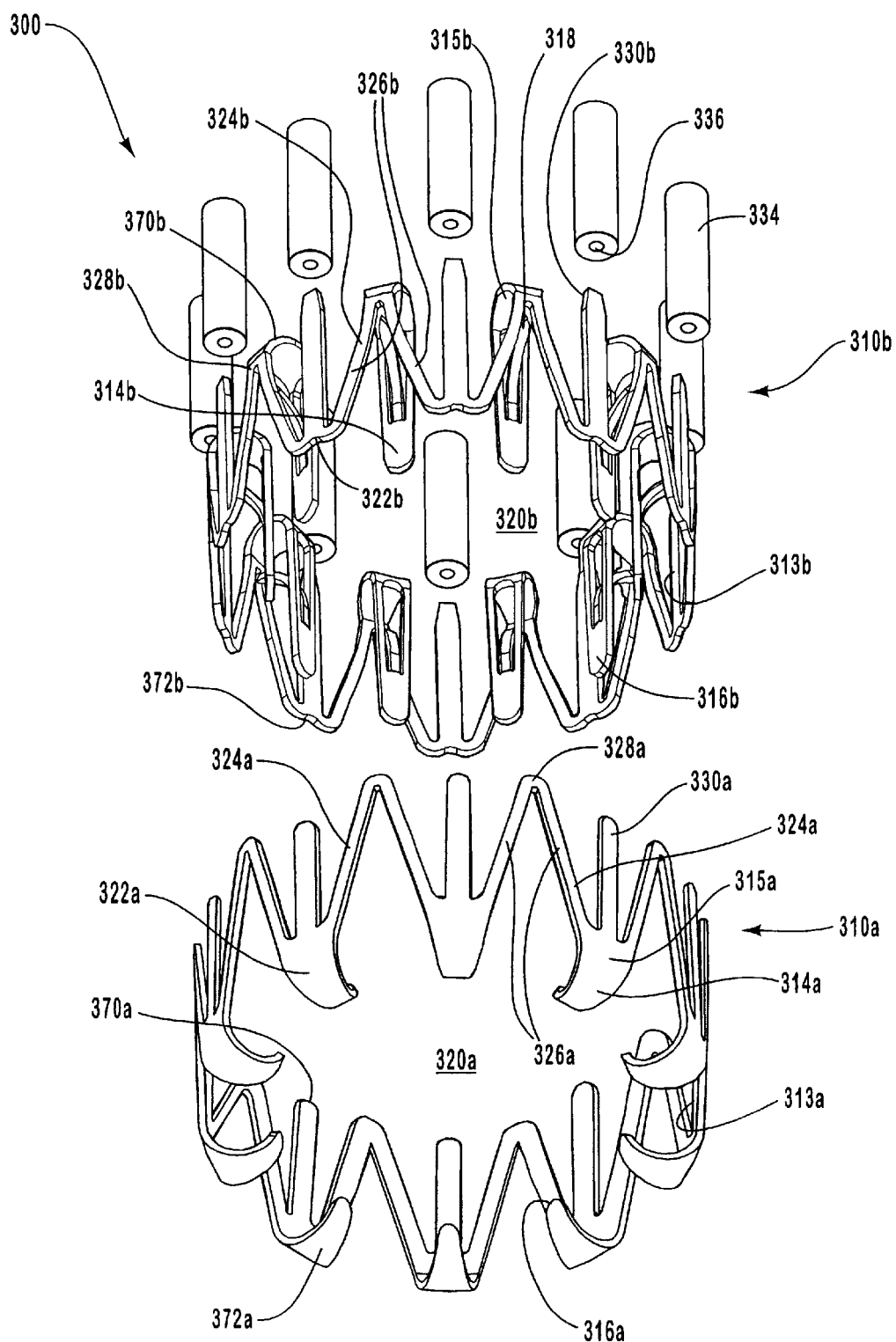
FIG. 1A is an exploded perspective view of a preferred embodiment of the paired, expandable anastomosis device with guides.

As shown in FIG. 1A, the anastomosis device comprises a first expandable ring and a second expandable ring. The first expandable ring is adapted to hold a first vessel, such as a target vessel, at an opening in the vessel. The second expandable ring is adapted to hold a second vessel, such as a graft vessel, at an opening in the vessel. The rings cooperate with guides so that after the graft and target vessels have been loaded onto the rings, the second ring may be brought together with the first ring to create an anastomosis. Once the two rings have been brought together, the rings are adapted to be linked together so that the rings expand and contract in unison.

Figure 3A:
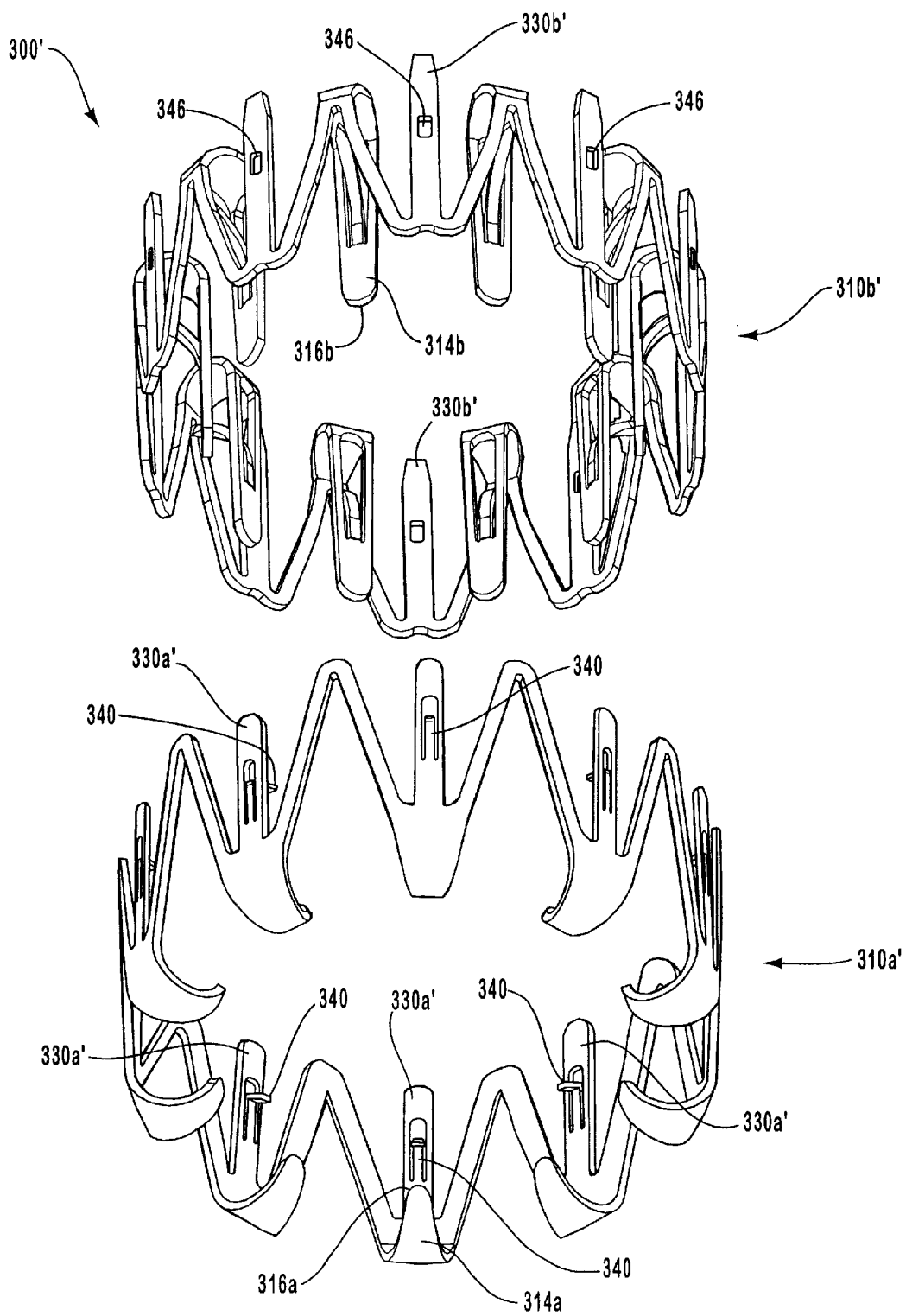
FIG. 3A depicts an exploded perspective view of an embodiment of the present invention with locking extensions on one ring and corresponding slots in the other ring.
Figure 3B:
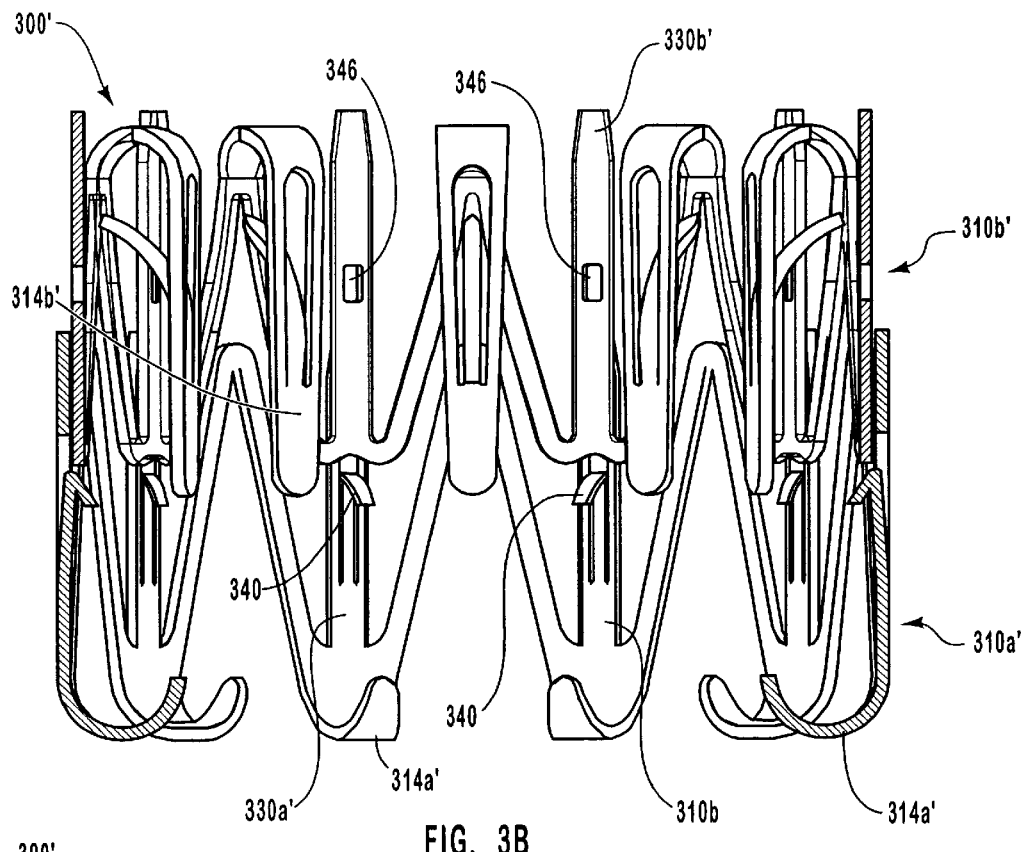
FIG. 3B is a cross-sectional view of the embodiment shown in FIG. 3A in a loading position.
Figure 3C:
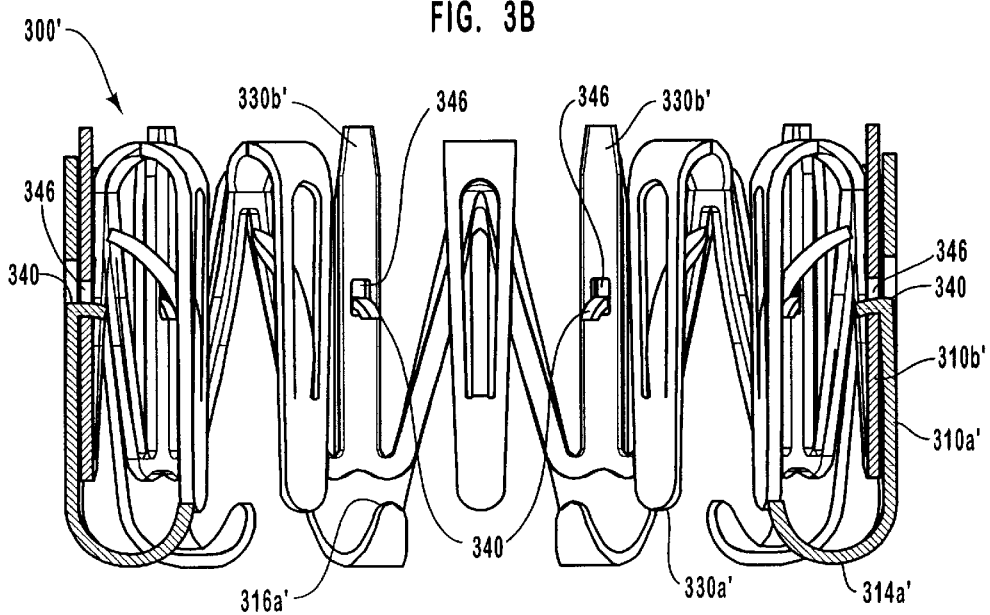
FIG. 3C is a cross-sectional view of the embodiment shown in FIG. 3A in an anastomosis position.
Figure 4A:
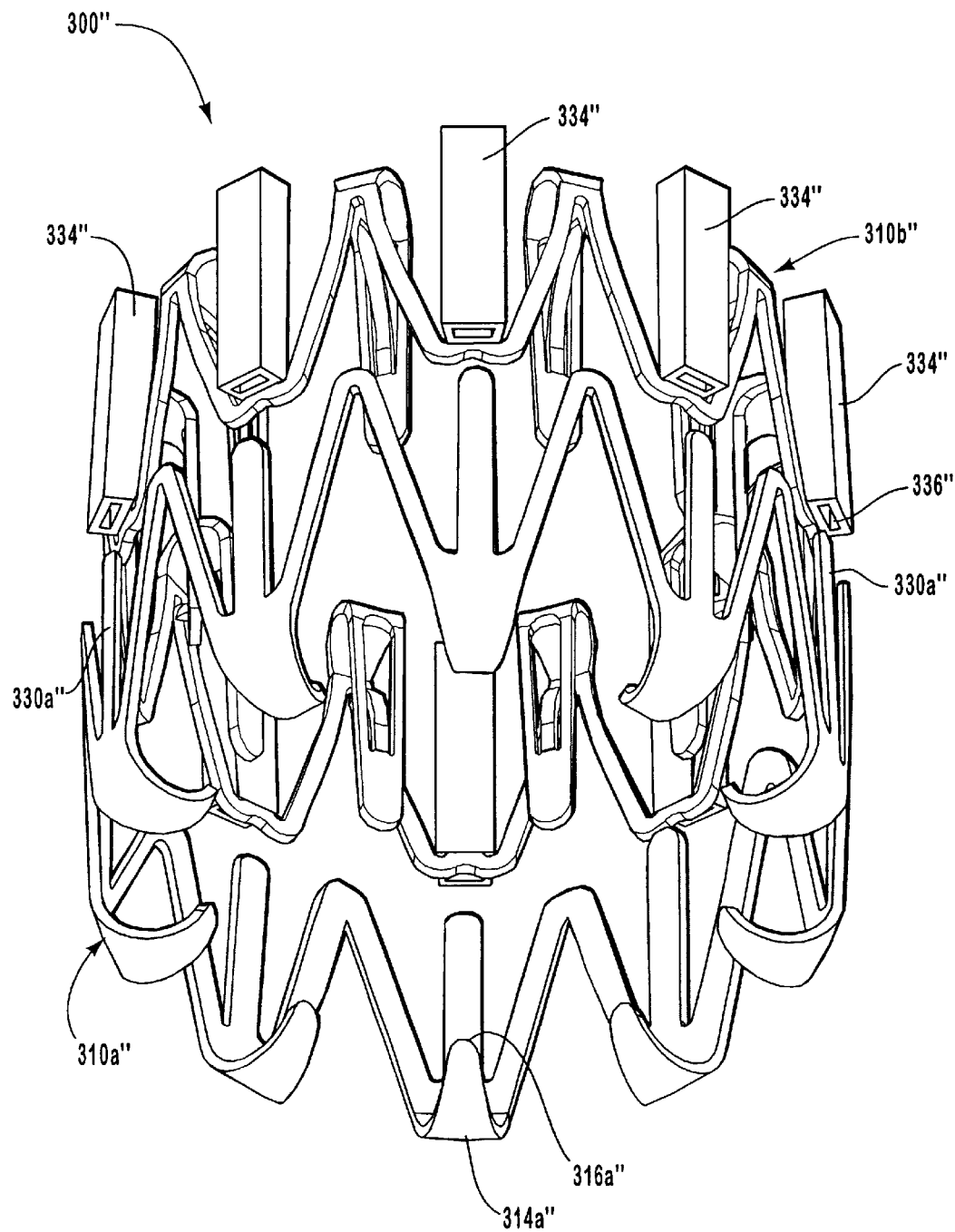
FIGS. 4A–4B are perspective views of an alternative embodiment of the anastomosis device having guides that are integral with one of the rings.
Figure 4B:
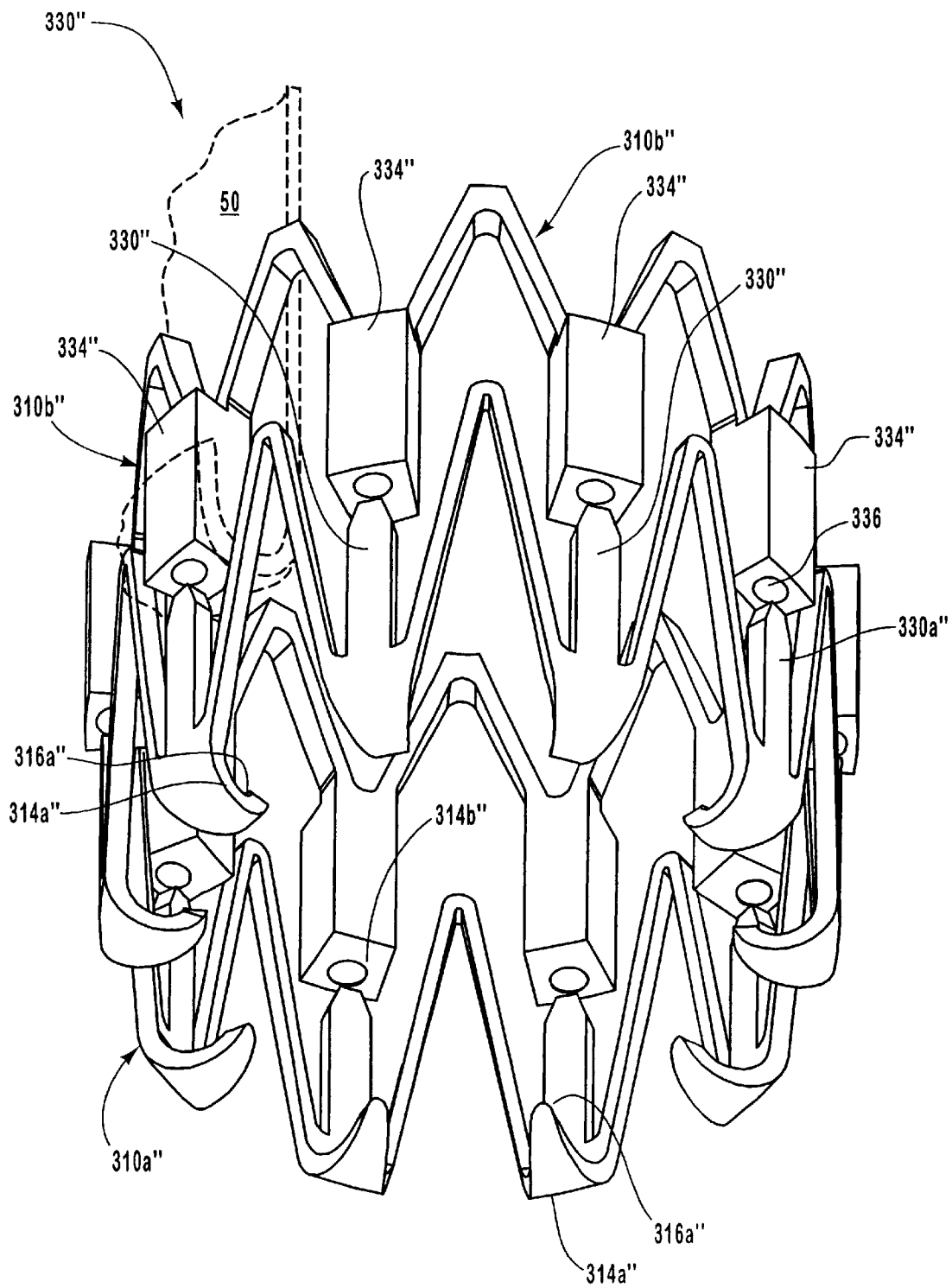

Anastomosis device 300 with guides and guideposts to link a pair of expandable rings together is shown at FIGS. 1A–1D. FIGS. 2A–2E depict the creation of an anastomosis opening in a vessel and the placement of anastomosis device 300 using an external operator 700". FIGS. 3A–3C depict an alternative embodiment of the anastomosis device having a ring with locking extensions positioned to slide into slots in the other ring. FIGS. 4A–4B depicts another embodiment of the anastomosis device in which one of the expandable rings is integral with a plurality of guides. FIGS. 5A–5F depict additional embodiments of the expandable rings. The anastomosis device may be used in combination with an attachment actuation device as depicted in FIGS. 6A–6C. Alternatively, the anastomosis device of the present invention may be utilized in combination with an attachment actuator of an external operator as depicted in FIGS. 7A–7F.

In the embodiment shown in FIG. 1A, first ring 310a is adapted to support a first vessel, such as a target vessel 20. First ring 310a has a generally annular shape and a plurality of holding surfaces or tabs 514a that define an opening, first ring opening 320a, which has a generally circumferential contour. The internal diameter of first ring opening 320a is such that the corresponding portion of the vessel to be anastomosed can fit therein. First ring opening 320a is generally round, however, the opening may also be ellipsoidal or ovoid.

First ring 310a comprises a plurality of connected flexible segments 324a each with two arms 326a joined by a flexible segment joint 328a. Arms 326a and flexible segment joints 328a form V-shaped flexible segments 324a. Each flexible segment 324a is attached to an adjoining flexible segment by a connecting joint 322a. First ring 310a further includes guideposts 330a adapted to slide into and frictionally engage with guides 334. The operation of the guides and guideposts is discussed in more detail below. First ring 310a has a first end 370a and a second end 372a and defines a first ring opening 320a. First ring 310a is an example of a first ring means for providing support for a first vessel at a first vessel opening.

As shown in FIG. 1A, holding tabs 314a extend integrally from first end 370a at connecting joints 322a. Holding surfaces or tabs are intended to hold the everted contours of the structures being anastomosed. More particularly, a portion of the target vessel defining a vessel opening is everted through ring 310a and held by holding tabs 314a. Each holding tab 314a extends radially inward and has a base 315a that extends from the ring. Bases 315a preferably curve radially inward with an U-shape. Holding tabs 314a are preferably wider at bases 315a than at the tips 316a opposite the bases 315a. Tips 316a–b are preferably rounded as shown to minimize the potential for penetration. Since, as discussed below, the anastomosis is generally completed immediately after the target vessel is loaded onto one of the rings, the holding tabs hold the target vessel long enough without additional anchors such as barbs or hooks. Holding tabs 314a are an example of holding means for holding the first vessel at the first vessel opening.

Still referring to FIG. 1A, second ring 310b is adapted to support a second vessel, such as graft vessel 50. The graft vessel may be synthetic or autologous. Second ring 310b has a plurality of holding surfaces or tabs 314b that define a second ring opening 320b with a round shape that corresponds to the shape of first ring opening 320a. Like first ring opening 320a, second ring opening 320b is such that the corresponding portion of the graft vessel can fit therein, as shown in FIG. 1D. Note that while the configuration of the first and second rings are designed to specifically interact respectively with the target and graft vessel, all or part of their configurations can be reversed so that the first and second rings respectively interact with the graft vessel and target vessel.

Second ring 310b comprises a plurality of connected flexible segments 324b, each with two arms 326b joined by a flexible segment joint 328b. Arms 326b and flexible segment joints 328b form V-shaped flexible segments 324b. Each flexible segment 324b is attached to an adjoining flexible segment by a connecting joint 322b. Second ring 310b has a first end 370b and a second end 372b. Second ring 310b is an example of a second ring means for providing support for a second vessel at a second vessel opening.

Holding tabs 314b extend integrally from first end 370b at flexible segment joints 328b. Holding tabs 314b are adapted to securely hold a portion of the graft vessel that defines an opening after the portion has been everted through ring 310b. In the embodiment shown in FIGS. 1A–1D, each holding tab 314b has a length that is about equal to the width of second ring 310b. Each holding tab 314b extends radially inward and has a base 315b that extends from the ring so that each holding tab 314b is opposite from arms 326b and guideposts 330b. Bases 315b are preferably U-shaped and curve radially inward toward the center of the expandable ring. The holding surfaces or tabs 314b are preferably wider at bases 315b, but narrower than bases 315a of first ring 310a. As with the holding tabs of the first ring, holding tabs 314b preferably terminate at rounded tips 316b that are rounded to minimize the potential for penetration. Holding tabs 314b are an example of holding means for holding the second vessel at the second vessel opening.

Each holding tab 314b of second ring 310b has a hook or barb 318 to prevent graft vessel 50 from slipping off holding surfaces 314b after graft vessel 50 has been loaded onto holding tabs 314b. Hooks 318 are an example of anchor means for more securely anchoring a vessel on the holding means.

Figure 1B:
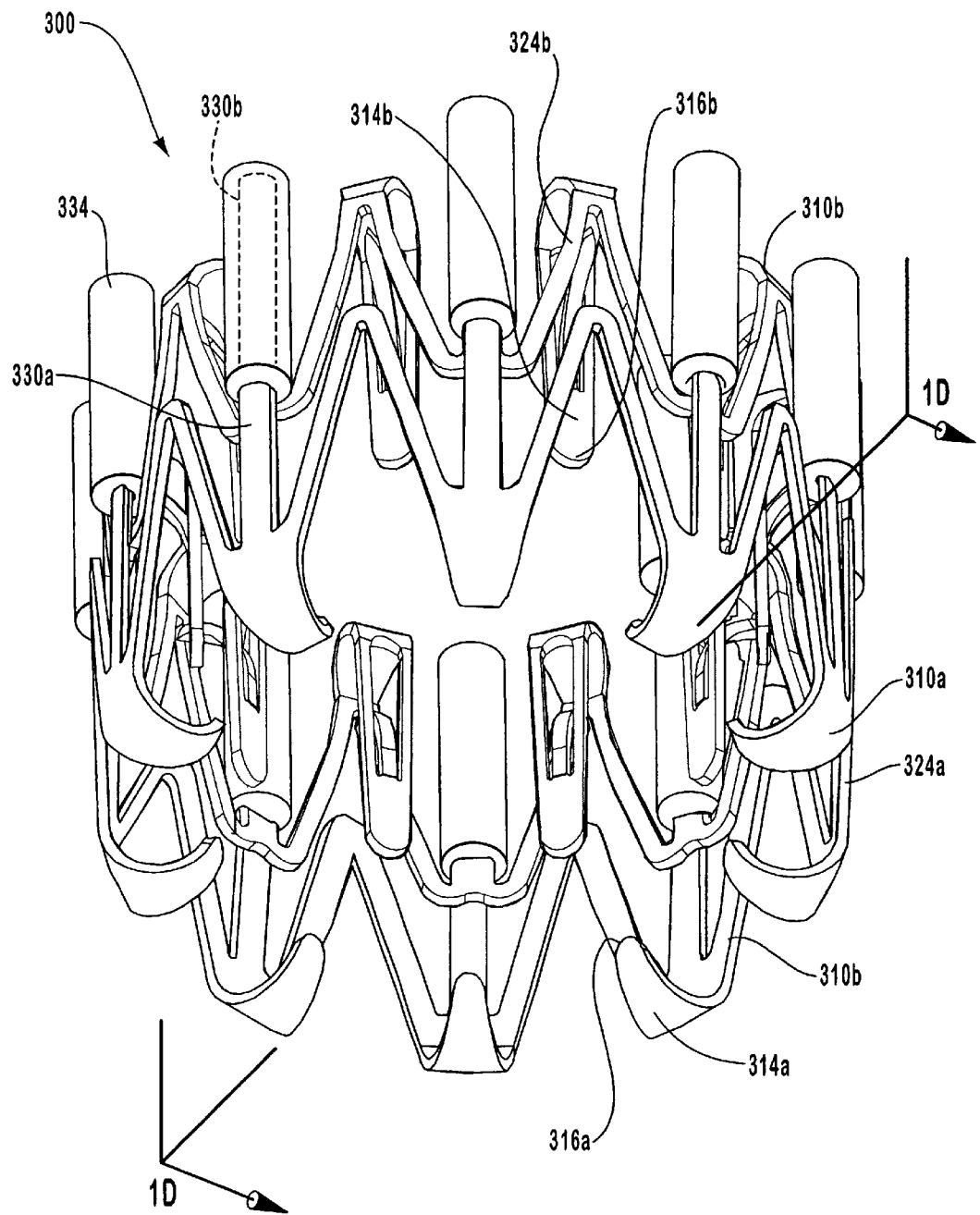
FIG. 1B is a perspective view of the anastomosis device depicted in FIG. 1A assembled and in the loading position.
Figure 1C:
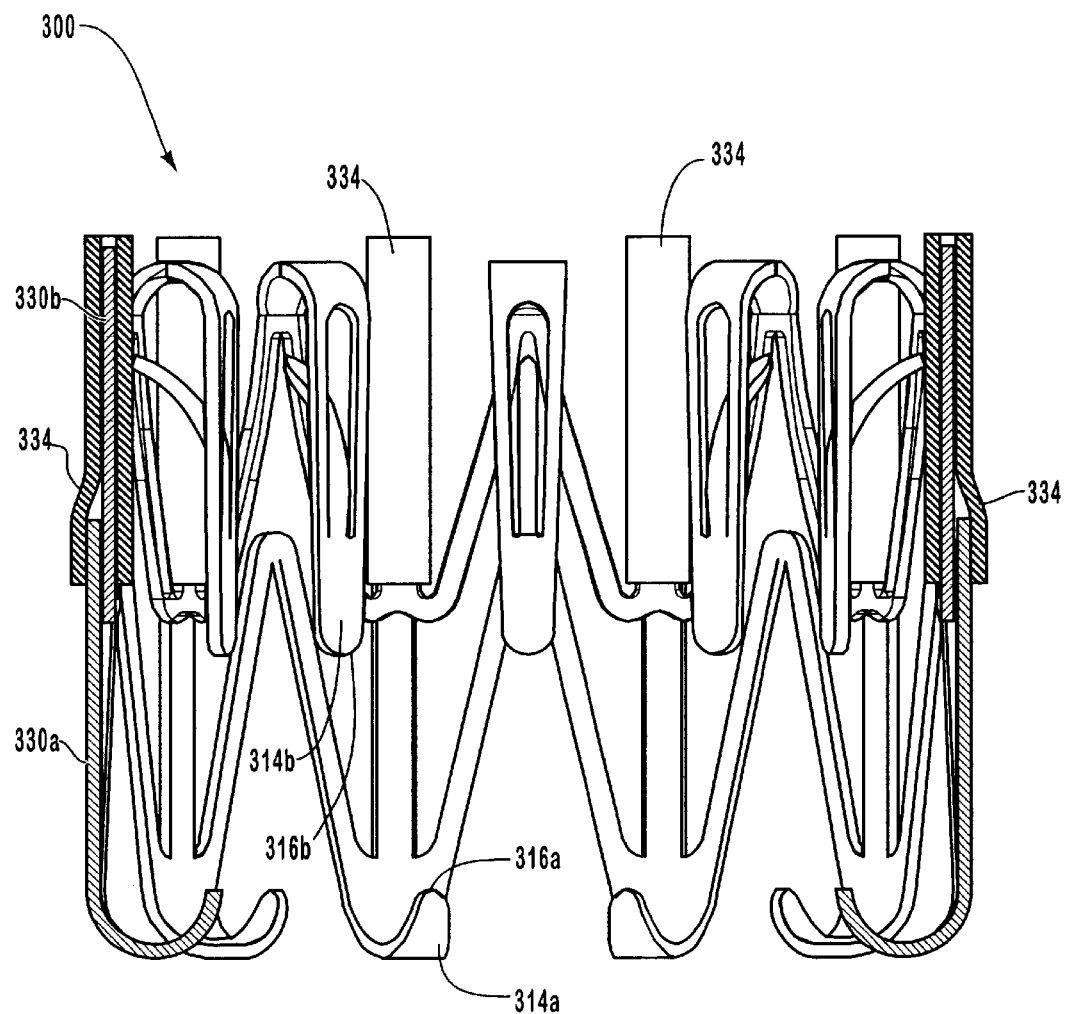
FIG. 1C is a cross-sectional view of the anastomosis device shown in FIG. 1B.
Figure 1D:
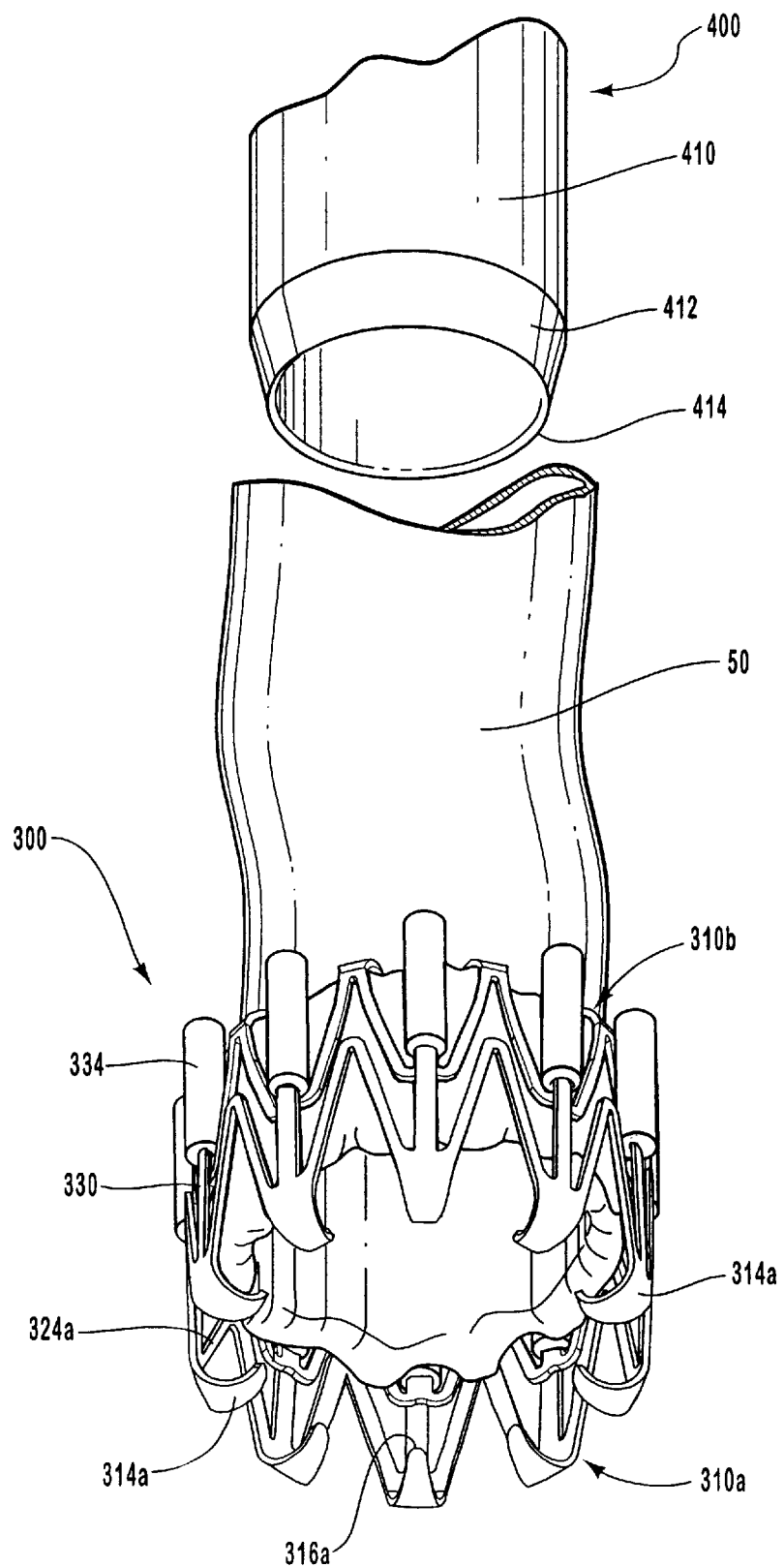
FIG. 1D is a perspective view of the anastomosis device shown in FIG. 1B with a graft vessel loaded onto the holding surface of the first expandable ring and a cutter positioned to be loaded into the lumen of the graft vessel.

Anastomosis device 300 is shown in FIGS. 1B–1C in a loading position before graft vessel 50 has been loaded onto holding tabs 314b of second ring 310b. As shown in FIG. 1D, a graft vessel 50 is loaded onto second ring 310b. The graft vessel may be synthetic or auotologous.

The holding surfaces such as holding tabs 314a–b are preferably configured in a way such that they are not exposed to blood flowing through the anastomosed structures. Blood vessels have an internal layer, called the intimal layer and an external layer called the adventitial layer. The holding surfaces are positioned to capture everted tissue defining an opening in a blood vessel so that the holding surfaces and rings contact the adventitial layer of the blood vessel. When the rings are moved together, to an anastomosis position, the intimal layer of the portion of the first vessel defining a first vessel opening contacts the intimal layer of the portion of the second vessel defining a second vessel opening. Stated otherwise, the holding tabs contact only the exterior of the everted vessel tissue and no portion of the device is exposed in the vessel lumens.

As shown in FIG. 1C, holding tabs 314a–b are positioned such that as the rings are brought towards each other, each holding tab 314b is positioned opposite from the spaces between holding tabs 314a in a mated configuration. When referring to the relative configuration of the holding tabs in opposing rings, the terms "mated or interdigitated configuration" describe a configuration in which each one of the holding tabs in a ring can generally fit in or at least be opposite the space between two neighboring holding tabs in the opposing ring when such rings are close enough. While other configurations are possible, the holding tabs in each ring are preferably oriented relative to the holding tabs in the other ring in such a mating configuration. Examples of interdigitated configurations are provided below.

As shown in FIG. 1A, anastomosis device 300 further comprises guides 334 with guide apertures 336. Guideposts 330a–b of first and second rings 310a–b are sized to slide into guide apertures 336. Guideposts 330a of first ring 310a extend from connecting joints 322a, opposite holding tabs 314a. Guideposts 330b of second ring 310b extend from flexible segment joints 328b. As shown in FIGS. 1B and 1C, the rings are held in an initial loading position with the rings offset from each other by the use of the guides and guideposts.

As shown in FIGS. 1B–1C, guides 334 position rings 310a–b in an initial loading position. In the initial loading position, the full length of each guidepost 330b of second ring 310b has been inserted into guides 334. Guideposts 330a of first ring 310a are partially inserted into guides 334 so that the rings are offset from each other. As shown in FIG. 1C, in the loading position, holding tabs 314a are sufficiently spaced apart from holding tabs 314b to permit graft vessel 50 to be everted through ring 310b and loaded onto holding tabs 314b. Additionally, in the loading position, holding tabs 314a–b are sufficiently spaced apart so that the tissue defining an opening in the target vessel may be everted onto holding tabs 314a and brought into contact with graft vessel 50.

Guides 334 are positioned to provide guided coaxial movement of the rings relative to each other so that the target vessel may be brought into contact with the graft vessel. Guides 334 permit the relative approach of the two rings as guideposts 330a are moved into guides 334, bringing ring 310b towards ring 310a. More particularly, guides 334 enable rings 310a–b to be brought together in a manner such that second ring 310b is moved in a fixed parallel orientation relative to first ring 310a. In the anastomosis position, rings 310a–b are compressed together and the graft vessel is anastomosed to the target vessel. Guides 334 in combination with guideposts 330a–b are an example of guide means for guiding the movement of one ring relative to the other ring.

The guides also operate to structurally link the two rings together so that while the rings expand and contract, the anastomosis remains intact. Guide apertures 336 are sized to frictionally engage guideposts 330a–b so that first ring 310a and second ring 310b remain in the anastomosis position, even as the rings expand and contract. More particularly, guide apertures 334 are sized such that, after the rings are compressed together, significant force is required to move one ring away from the other ring. The frictional engagement of guides 334 with guideposts 330a–b also enables rings 310a–b and the anastomosis to contract and expand in unison in response to change in fluid pressure through the target and graft vessels. Guides 334 in combination with guideposts 330a–b are examples of locking means for locking the first ring and second ring together such that the first vessel and the second vessel remain anastomosed together.

To ensure sufficient compression of rings 310a–b, guides 334 and guideposts 330 are preferably sized so that when rings 310a–b are approximated to an anastomosis position, the holding tabs of one ring are sufficiently close to the holding tabs of the second ring to create a blood-tight anastomosis of the graft and target vessels. An example of a suitable compression is provided by an anastomosis device with holding tabs of a length such that the tips slightly extend into the space between the holding tabs of the opposite ring in an interdigitated configuration. The rings may also be designed for further compression such that holdings surfaces or tabs 314b further enter the space between adjacent holding surfaces or tabs 314a. Of course, the rings are preferably designed such that the rings are brought together without penetrating target vessel 20 or graft vessel 50.

Other interdigitated configurations are also possible. The rings may be designed so that when the rings are compressed together, the tips of the holding tabs of one of the rings terminate in approximately the same plane as the tips of the holding tabs of the other ring. Alternatively, the rings may be adapted such that, in the anastomosis position, the holding tabs of one ring are slightly offset from the holding tabs of the other ring. The rings are accordingly sized to have an anastomosis position that compresses down to the ideal spacing between the anastomosis sides while providing holding surfaces that have sufficient surface area to capture the tissue in an everted configuration.

As can be seen from FIG. 1D, a graft vessel 50 is loaded onto holding tabs 314b of ring 314 while a cutter 400 is positioned to be loaded into the lumen 58 of graft vessel 50. Cutter 400 includes a cutting tube 410 that terminates at a cutting knife 412 with a cutting edge 414. Once cutter 400 is positioned within graft vessel 50 then the combination of anastomosis device 300, graft vessel 50 and cutter 400 are ready for use with anvil apparatus 200 to form an anastomosis. This combination is referred to herein as ring and cutter assembly.

FIGS. 2A–2E depict the use, in sequential order, of an anastomosis device 300 in combination with a cutter 400, anvil 210 and an attachment actuator 600" of an external operator 700". The operation of the external operator 700" is described in more detail below with reference to FIGS. 7A–7F. To optimally present this sequence, FIGS. 2A–2E are cross-sectional views.

Figures 2A, 2B:
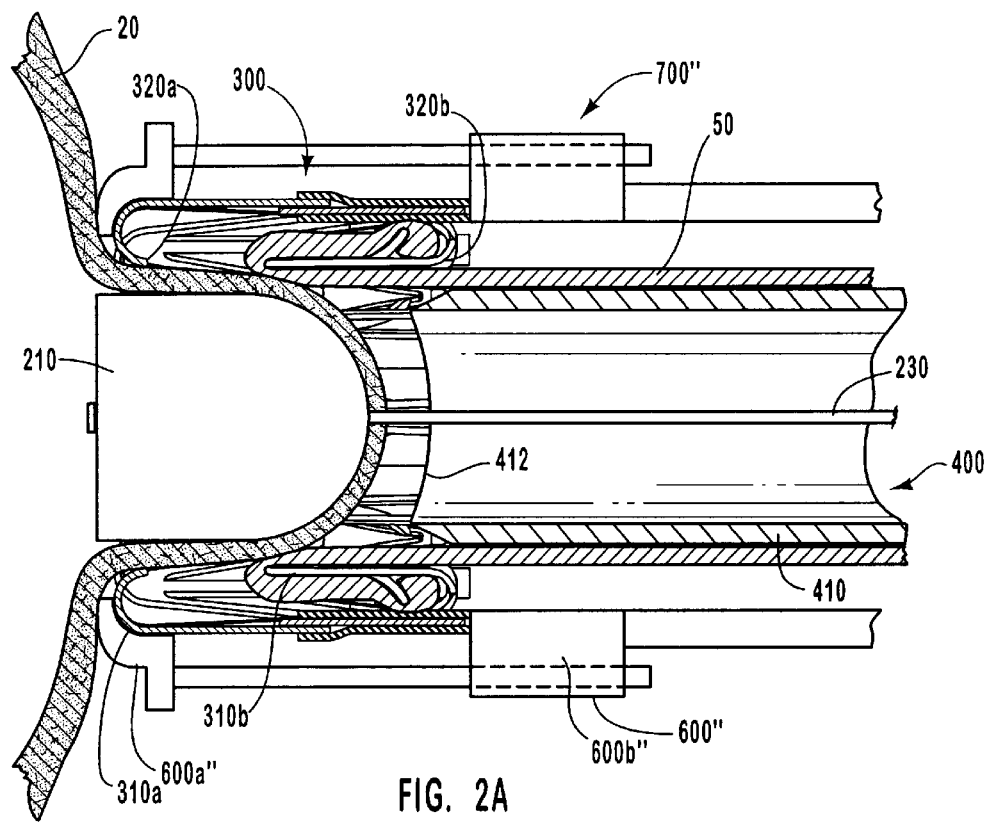
FIG. 2A is a cross-sectional view of the anastomosis device shown in FIG. 1A as anvil apparatus distends a target vessel into the anastomosis device.
FIG. 2B is a cross-sectional view of the anastomosis device shown in FIG. 2A in the next phase as a cutter and an anvil are engaged to form an opening in the vessel.

FIG. 2A depicts a graft vessel 50, loaded onto ring 310b. FIG. 2A also depicts anvil 210 being pulled against the intima or interior of the vessel wall such that target vessel 20 is sufficiently distended to permit target vessel 20 at anastomosis site 10 to be pulled into anastomosis device 300 through first ring opening 320a. Cutter 400 also is shown in FIG. 2A extending through second ring opening 320b about half way through anastomosis device 300 as cutter 400 is approximated with the portion of the target vessel 20 distended by anvil 210.

FIG. 2B depicts the formation of a first vessel opening 24 in the wall of the first vessel. First vessel opening 24 is formed by pulling anvil pull 230 through cutter 400 with sufficient force to enable anvil 210 to advance target vessel 20 against cutting edge 414. After the cut has been made then a cut portion 25 of the wall of target vessel 20 remains on spherical engaging end 212 of anvil 210 while the portion 26 of the target vessel that now define first vessel opening 24 rests on anvil landing 214.

Figure 2C:
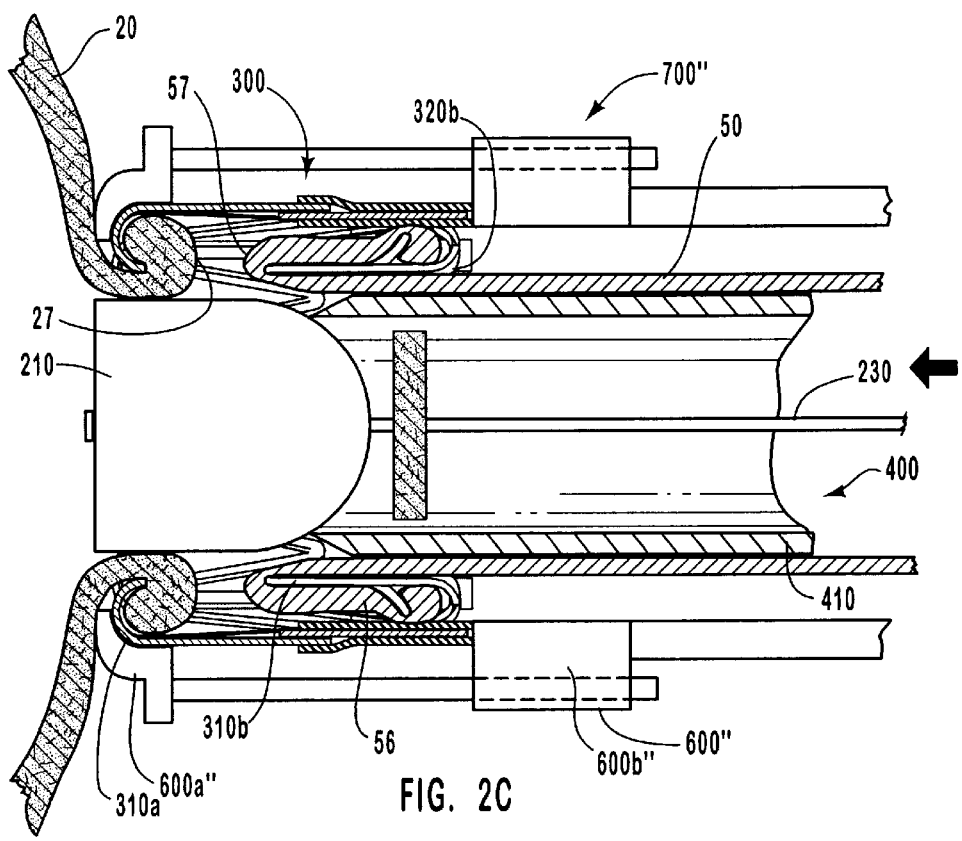
FIG. 2C is a partial cross-sectional view of the anastomosis device shown in FIG. 2B in the next phase as the graft vessel everts the portion of the target vessel defining the first vessel opening.
Figure 2D:
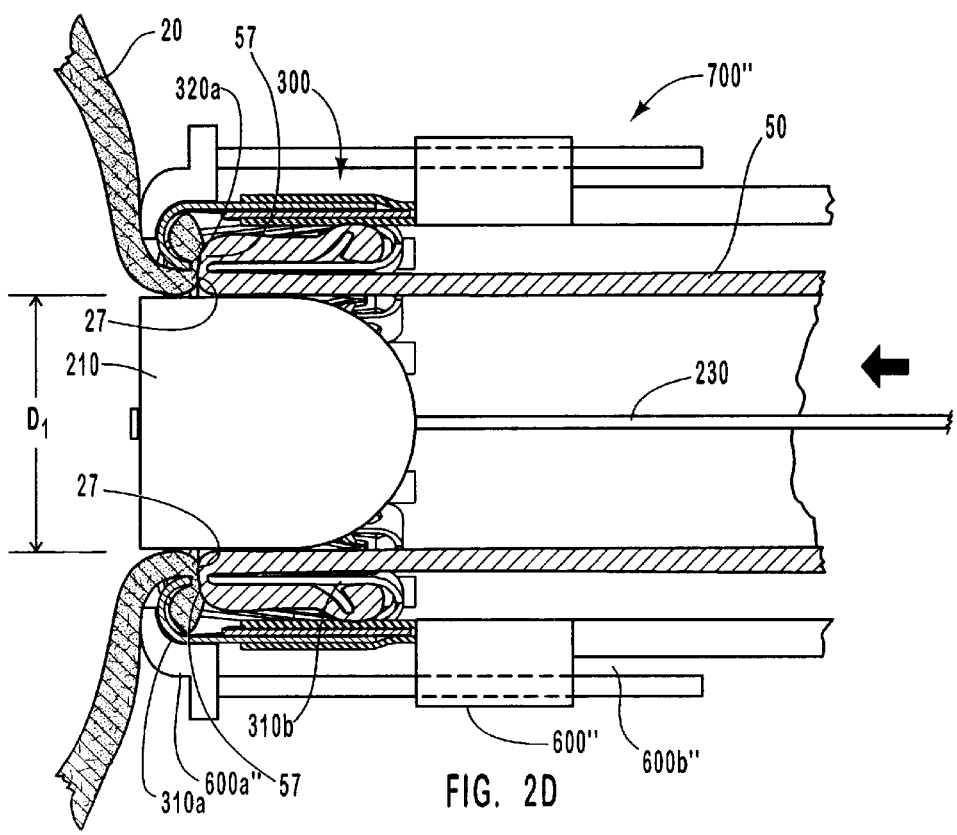
FIG. 2D is a cross-sectional view of the anastomosis device shown in FIG. 2A in the next phase after the second compression plate has been compressed towards the first compression plate such that the everted graft vessel contacts the everted target vessel.

FIG. 2C depicts anastomosis device 300 as it is being compressed and as portion 26 defining vessel opening 24 is being everted. FIGS. 2C–2D depict the rings being brought together by an attachment actuator 600" of an external operator 700". Attachment actuator has a first ring engager 600a" and a second ring engager 600b" adapted to hold first and second rings 310a–b in a fixed orientation relative to each other and to bring rings together in this fixed orientation. In the embodiment shown in FIGS. 2A–2E, attachment actuator 600" has actuating guides 640" that guide one ring engager toward the other ring engager to bring the expandable rings together. Each ring engager 600a"–b" has a latch (not shown) that enables the ring engagers to be released once the anastomosis is complete. The rings may, alternatively, be brought together by an attachment actuation device, which is described in more detail below with reference to FIGS. 6A–6C.

Note that the everted portion 56 of graft vessel 50, more particularly the portion 57 opposite runded tips 316 of holding tabs 314b, is urged against portion 26 that defines first target vessel opening 24 in a manner such that portion 26 is being everted. This eversion process is augmented by landing 214 of anvil 210 which allows portion 26 to rest on landing 214 and be plowed upward by everted portion 56. The length of portion 26 is sufficient for this eversion process since vessel 20 was distended and pulled into the snap-fit anastomosis device by the action of anvil 210.

FIG. 2D depicts anastomosis device 300 after compression. More particularly, ring 310b has been moved toward ring 310a by sliding guideposts 330b on guides 334. Note that the everted portion 56 of graft vessel 50, more particularly the portion 57 opposite from the rounded tip 316b, is urged against portion 26 that defines first target vessel opening 24 in a manner such that portion 26 has been everted. The end result is that the portion 27 opposite from rounded tip 316a is held in contact with the portion 57 of vessel 50 opposite from distal rounded tip 316b.

During anastomosis, the rings are preferably held in an initial, radially compressed position by attachment actuator 600" of external operator 700" or attachment actuation device 600'. In this radially compressed position, each ring opening has an initial diameter. Once the vessels are anastomosed together, the rings are released by the attachment actuator and spring radially to a deployed position. In the deployed position, the rings have a greater diameter, stretching the vessel openings at the anastomosis site.

Figure 2E:
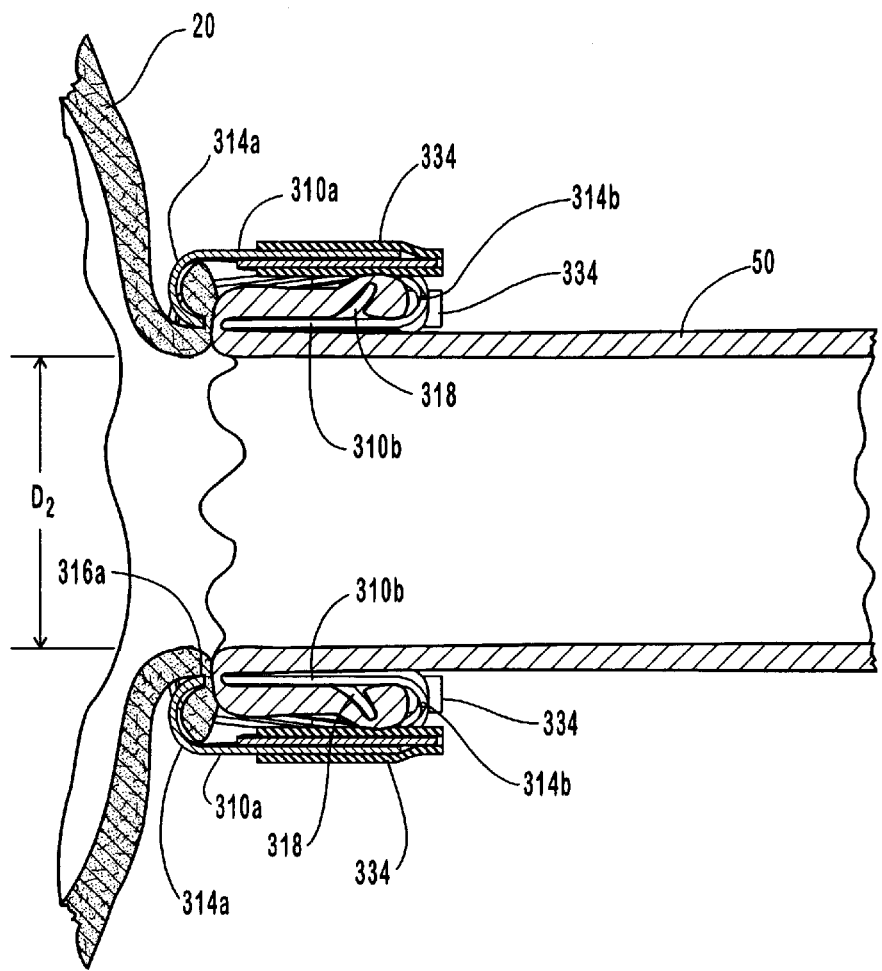
FIG. 2E is a cross-sectional view of the anastomosis device shown in FIG. 2A with the anastomosed structure after the anvil apparatus and the cutter have been removed.

This radial expansion is best seen in FIGS. 2D–2E. The rings preferably spring open sufficiently so that, at the anastomosis site, the vessel openings have a diameter equal to or greater than the diameter of the graft vessel, thus minimizing restriction at the anastomosis. For example, for a graft vessel having a diameter of about 5 mm the initial diameter of the ring openings may be about 4 mm and the diameter of the ring openings after deployment may be about 6 mm. As shown in FIG. 2D, external operator 700 holds rings 310a–b in an initial state with a diameter D1. When anastomosis is complete and external operator 700 releases anastomosis device 300, rings 310a–b radially expand to a greater diameter, D2, as shown in FIG. 2E.

After rings 310a–b have been brought together to join portion 26 of target vessel 20 that defines first vessel opening 24 to portion 56 of second vessel 50 that defines graft vessel opening 54, then first vessel 20 and second vessel 50 are anastomosed together and are in fluid communication. Note that holding tabs 314a–b hold the vessels in place without penetration and without contacting the interior of the vessels. Anvil apparatus 200 and cutter 400 have been removed upon the completion of the procedure through lumen 58 of graft vessel 50. Once the anastomosis is complete, guideposts 330a–b remain stationary in guides 334 after being compressed due to frictional engagement.

There are significant advantages to combining vessels in accordance with the device described above, especially in a manner such that there is at least partial eversion and contact between the everted surfaces of the vessels. Another advantage is that there is no penetration of the portions of the vessels defining the vessel openings or at least no penetration of the target vessel. Of course, the anastomosis is fluid tight to normal systolic pressure and remains intact under stress. Since the everted portions 26 and 56 respectively cover the holding tabs 314*a–b*, exposure of subintimal connective tissue is minimized. The rings create an anastomosis that is morphologically satisfactory, including complete eversion of the receiving target vessel intima with apposition to the graft vessel. Further, everted portions 26 and 56 are in intima-intima contact and no cut portion is significantly exposed to the blood flow that is to circulate through the anastomosed structures.

Furthermore, the rings create an anastomosis without any placing any foreign material into the anastomosed vessels and the interior of the vessels are not exposed to any foreign material. As a result, the thrombogenic potential is minimized.

Also, as discussed above, the rings radially expand upon initial deployment. The radial expansion of the rings enables the anastomosis to have a diameter that is larger than the initial opening in the vessel. It may expand enough to be equivalent to the diameter of the anastomosed vessels. Thus, a smaller incision in the target vessel is required. Because a smaller incision is required, smaller instruments may be used to create the opening in the target vessel and to place the anastomosis device. For example, the anvil and the cutter may be smaller than would otherwise be required. As a result the invasiveness of the procedure is minimized. By radially expanding upon release to create an opening at least equal in diameter to the graft vessel, the present invention also minimizes the restriction at the anastomosis and potential resulting complications such as thrombosis and neointimal hyperplasia.

The rings are also capable of expanding and contracting with changes in the fluid pressure in the anastomosed vessels. For example an anastomosis device which joins two blood vessels will expand and contract with systole and diastole. The rings can expand and contract while the holding tabs maintain the anastomosis. By expanding and contracting with changes in fluid pressure, the anastomosis device of the present invention minimizes flow disturbances as the blood flow approaches the anastomosis site. This feature also serves to minimize thrombosis and neointimal hyperplasia.

In addition to the results achieved, there are also significant procedural advantages. The method does not require temporary occlusion of blood flow to the target vessel. The second ring may be pre-loaded with the graft vessel so that the steps disclosed above in connection with FIGS. 2A–2E may be accomplished simultaneously or in quick succession. By pre-loading the graft vessel and simultaneously cutting a target vessel opening and loading the target vessel, the rings may be brought together to create the anastomosis without blocking blood flow through the target vessel. Also, the anastomosis can be reliably created. The anastomosis utilizing the paired rings of the present invention is rapidly achieved and eliminates the need for highly skilled suturing. For example, once the anvil pull extends through the wall of the vessel, the anastomosis procedure can be accomplished in as little as 30 seconds when rings 310*a–b* are used to join the vessels.

Manual manipulation may be utilized to achieve the steps shown in FIGS. 2A–2E, however, mechanization is preferred. More particularly, anvil pull 230 may be manually pulled as cutter 400 is held or manually advanced. Additionally, the anastomosis device may be manually compressed in some embodiments. However, the paired rings of the present invention are preferably used in combination with an intraluminally directed anvil apparatus such as the apparatus disclosed in U.S. Pat. No. 6,248,117, which is hereby incorporated by reference. Other intraluminally directed anvil apparatus are disclosed in U.S. patent application Ser. No. 09/737,200 and Ser. No. 09/460,740 which were previously incorporated by reference. The paired rings may also be used in combination with an externally directed apparatus, such as those disclosed in U.S. patent application Ser. No. 09/736,781, filed Dec. 14, 2000 and entitled Externally Directed Methods for Forming an Anastomosis Opening in a Vessel, U.S. patent application Ser. No. 10/003,985 filed on Oct. 31, 2001 and entitled Soft Anvil Apparatus for cutting Anastomosis Fenestra, and U.S. patent application Ser. No. 10/003,956 filed on Oct. 31, 2001 and entitled Externally Positioned Anvil Apparatus for Cutting Anastomosis Fenestra, which are hereby incorporated by reference. Alternatively, the anastomosis device may be used in combination with any suitable mechanical anastomosis techniques.

FIGS. 3A–3C depict an alternative embodiment of the anastomosis device, referred to herein as anastomosis device 300'. The two rings of anastomosis device 300' are structurally linked by locking extensions 340 in combination with slots 346. As shown in FIGS. 3A–3B, each locking leg 330*a'* of first ring 310*a'* has a locking extension 340. As shown in FIG. 3C, each locking extension 340 is positioned to lock into a corresponding slot 346 in a locking leg 330*b'* when rings 310*a'–b'* are brought together to the anastomosis position. Legs 330*b'* having slots 346 in combination with legs 330*a'* having locking extensions 340 are additional examples of locking means for locking the first ring and second ring together such that the first vessel and the second vessel remain anastomosed together. Alternatively, the expandable rings may be linked by any suitable device, such as clips, clamps or interlocking tabs. Sutures or adhesive may also be used to structurally link two rings together. Clips, clamps, interlocking tabs, sutures and adhesives are all further examples of locking means for locking the first ring and second ring together such that the first vessel and the second vessel remain anastomosed together.

As shown in FIGS. 3A–3C, anastomosis device 300' functions without guides such as the guides of the embodiment shown in FIG. 1A. Instead, rings 310*a'–b'* of anastomosis device 300' are adapted to be coupled by an attachment actuation device 600' as shown in FIGS. 6A–6C or attachment actuator 600 of external operator 700 as shown in FIGS. 7A–7E, both of which are discussed in more detail below. Attachment actuator 600 and attachment actuation device 600' have a first ring engager 600*a*, 600*a'* and a second ring engager 600, 600*b'* that are adapted to guide rings 310*a–b* from a loading position to an anastomosis position.

FIGS. 4A–4B depict an additional embodiment of the anastomosis device, referred to herein as anastomosis device 300". Guides 334" of anastomosis device 300" are integral with second ring 310*b"* and have holding surfaces 314*b*. Second ring 310*b"* is preferably made of plastic and integrally molded with guides 334. Ring 310*b"* enables graft vessel tissue to be everted through ring 310*b"* and over holding surfaces 314*b"*.

Ring 310*a"* has guideposts 330" positioned to slide into guides 334". Guides 334" have apertures 336" that are sized to frictionally engage guideposts 330". FIG. 4B depicts a partial cross-section of a graft vessel 50 in phantom lines. Guideposts 330" in combination with guides 334" are an additional example of locking means for locking the first ring and second ring together such that the first vessel and the second vessel remain anastomosed together.

The graft vessel is everted through ring 310b" and over holding surfaces 314b". In the embodiment shown in FIG. 4B, ring 310b is designed such that the graft tissue is everted through ring 310b over holding surfaces 314b and onto the outer surface of guides 334". In this embodiment, guideposts 330a" are adapted to penetrate graft vessel tissue that has been everted through second ring 310b' and past guide apertures 336". After the graft vessel is loaded onto second ring 310b, guideposts 330a" penetrate the graft vessel and slide partially into guides apertures 336". Guideposts 330" in combination with guides 334" are an additional example of anchor means for more securely anchoring a vessel on the holding means.

As shown in FIGS. 4A–4B, holding surfaces 314b" are at the top of guides 334". As shown in FIG. 3A, each holding surface 314b" is a flat surface. Holding surfaces 314a"–b" of rings 310a"–b" of anastomosis device 300" are arranged so that when rings 310a"–b" are brought together to an anastomosis position, holding tab tips 316a" of first ring 310a" directly oppose holding surface 314b" of second ring 310b". Therefore, the graft and target vessels are pinched between tips 316a" and holding surfaces 314b" when rings 310a"–b" are in the anastomosis position.

Holding surfaces, such as holding tabs 314a–b depicted in FIG. 1A and holding surfaces 314b" depicted in FIG. 4A, can have a variety of shapes and arrays. A generally regular distribution on the anastomosis sides of rings 310a–b is preferred. Holding surfaces may also form a contiguous surface around a ring. For example, a suitable elastic band may be utilized as a ring having a contiguous surface.

In an alternative embodiment, the holding tabs are inclined towards the ring so that each holding tab clamps vessel tissue against the ring. In another embodiment, holding tabs of one of the rings are spike shaped or have pointed tips to better retain the graft vessel. The holding tabs are typically rather rigid, however, they may also be designed to elastically bend in such a way that the distal tips of such holding surfaces slightly swing about their respective bases.

The number of holding surfaces and their spacing may be varied as needed as long as the portions of the vessels defining the vessel openings can be maintained in an everted orientation. For example, the plurality of holding surfaces may include ten holding surfaces or tabs as shown in FIG. 1A. However, smaller or greater amounts may also be utilized, for example there may be from three to sixteen holding surfaces.

The guides may also be distributed in varying numbers and arrays. The guides may be movably connected to the rings. Alternatively, the guides may be integral with one of the rings. The anastomosis devices depicted in FIGS. 1A and 4A have ten guides. Alternative embodiments may include only two or more guides. The guides may extend from one or both of the rings at any appropriate location. The guides are preferably regularly distributed around the ring. Furthermore, the guides are preferably situated such that the portion defining the target vessel opening and the portion defining the graft vessel opening are joined without being penetrated as the first vessel and the second vessel are anastomosed together.

Figure 5A:
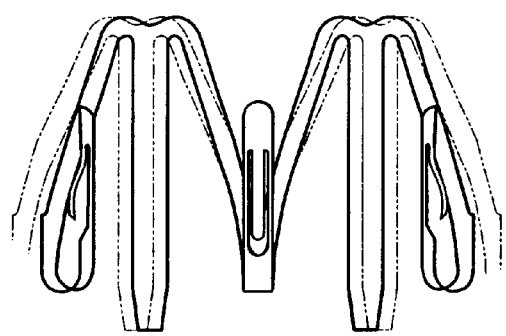
Figure 5B:
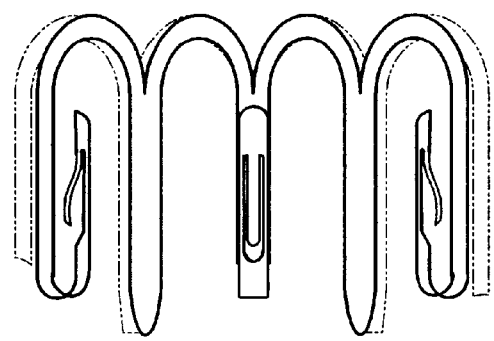
Figure 5C:
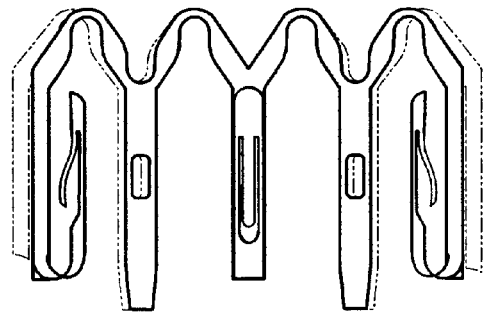
Figure 6A:
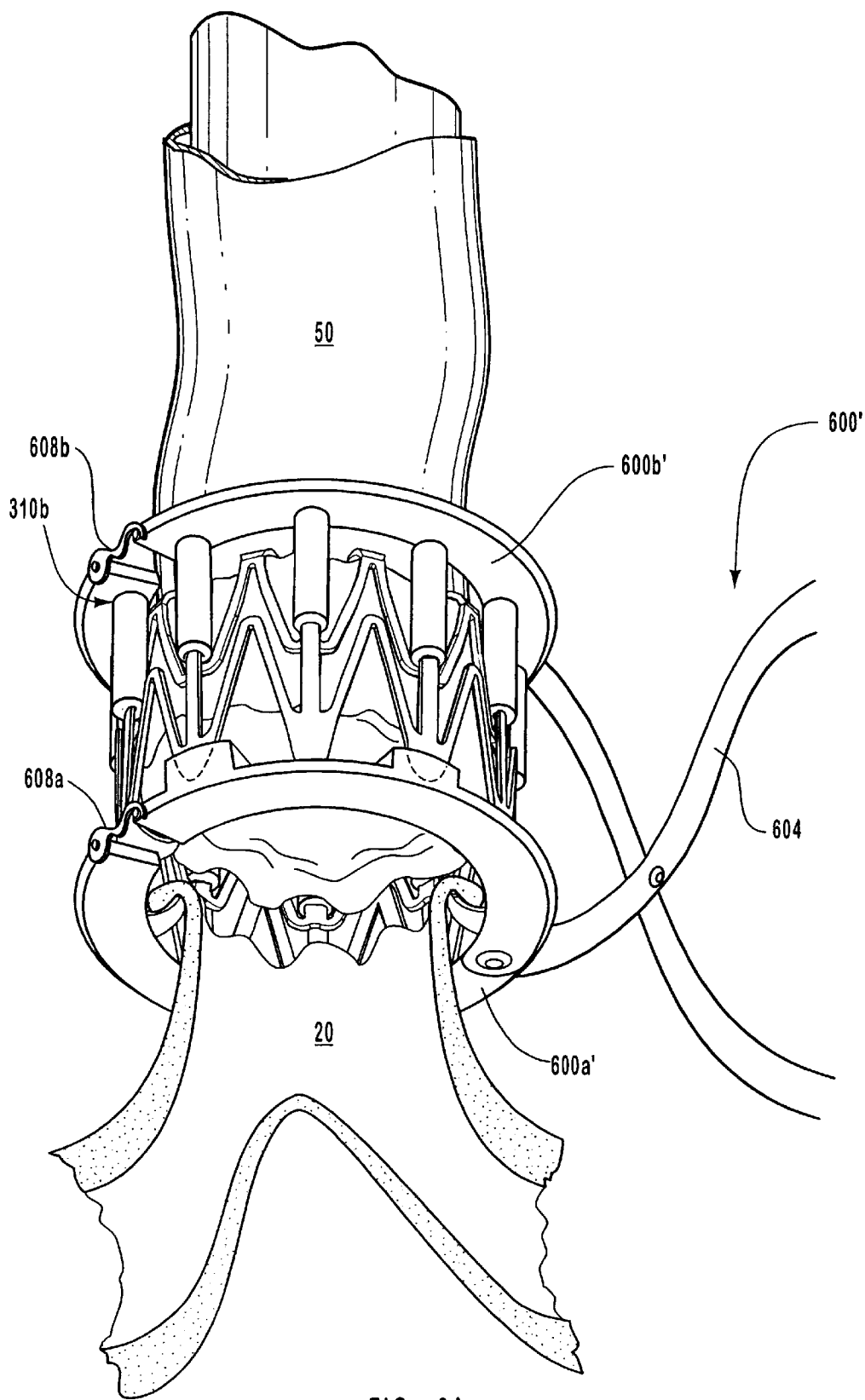
FIG. 6A is a partial cross-sectional view of the embodiment shown in FIG. 1A used in combination with an attachment actuation device.
Figure 6B:
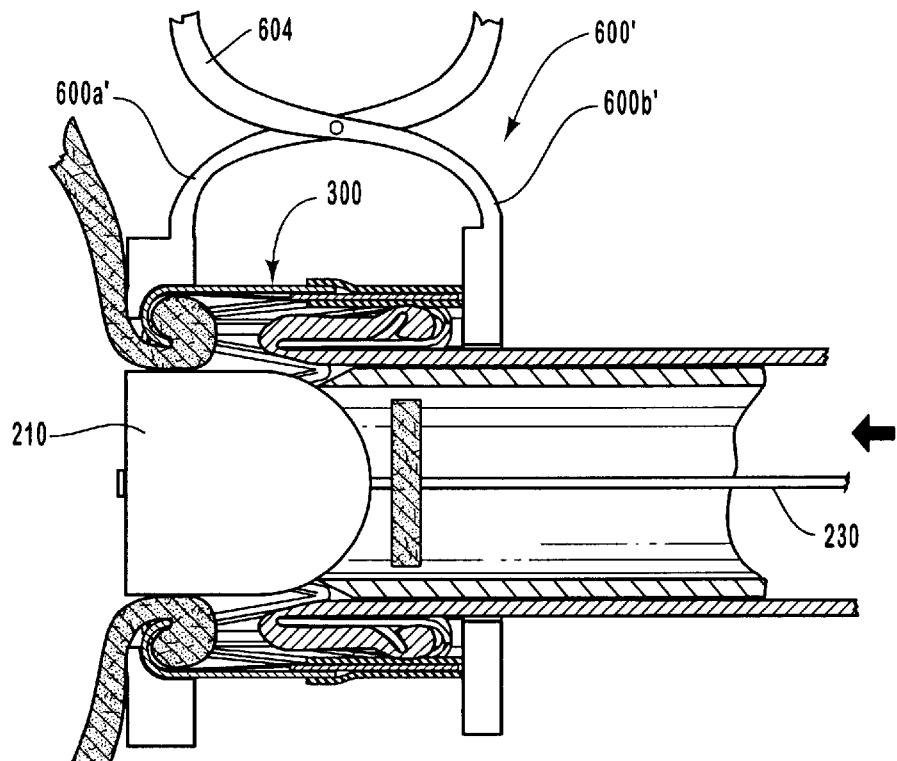
FIG. 6B is a perspective and partial cross-sectional view of the anastomosis device shown in FIG. 6A in the loading position.
Figure 6C:
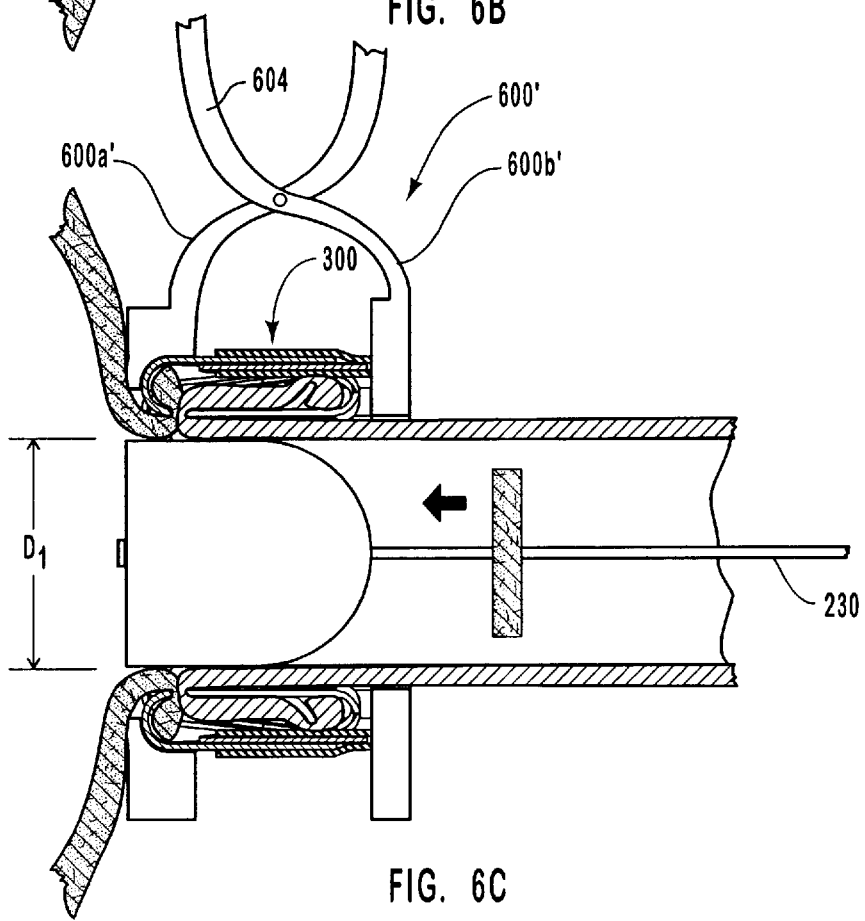
FIG. 6C is a cross-sectional view of the anastomosis device shown in FIG. 6B in the next phase after the first expandable ring has been compressed towards the second expandable ring by the attachment actuation device such that the everted graft vessel contacts the everted target vessel.

As depicted in FIGS. 5A–5E, the rings of the present invention may have flexible segments with a variety of shapes. The expandable rings may be formed of any shape of flexible segment that provides the rings with the capability to expand and contract with changes in fluid pressure. FIGS. 5A–5C depict alternative embodiments of the second ring. FIG. 5A is a partial view of V-shaped flexible segments 324 of the second ring 310a depicted in FIG. 1A. FIG. 5B depicts an expandable ring that comprises a series of U-shaped flexible segments. FIG. 5C depicts an expandable ring comprising a series of flexible segments which are made of plastic and have hinged portions of decreased thickness relative to adjacent portions.

FIGS. 5D–5F depict embodiments of the first ring with varied flexible segments. FIG. 5D depicts an expandable ring with U-shaped flexible segments. FIG. 5E shows a ring comprising flexible segments which have a configuration that is diamond shaped. The diamond shaped configuration is an example of a quadrilaterial configuration. FIG. 5F depicts an expandable ring with circular flexible segments. Alternatively, the rings may include spiral-shaped flexible segments, oval-shaped flexible segments, elliptical flexible segments and other flexible segments that have appropriate configurations.

The positioning of the anastomosis device and the operations of pulling or holding anvil pull 230, making an opening, and compressing the rings together, as described in connection with FIGS. 2A–2E, can be accomplished manually or with the aid of devices such as external anastomosis operator 700. The attachment actuation means need not be part of the same apparatus with the anvil pull engager and the cutter. This reduces the size of the instruments utilized.

FIGS. 6A–6C show an attachment actuation device or tongs 600' used to approximate rings 310a–b. Actuation device 600' has opposing ring engagers, a first ring engager 600a' and a second ring engager 600b', that respectively extend from attached handles 604a–b. Handles 604a–b are connected together at a hinge. Each ring engager 600a'–b' has a latch 608a–b that enables the ring engagers to lock onto expandable rings 310a–b so that anvil 210 can be pulled through second ring opening 320b and distend the wall of vessel 20 into expandable anastomosis device 300. While the tissue of vessel 20 is cut and everted onto holding surfaces 314b", tongs 600' are closed. Once the anastomosis is complete, latch 608a'–b' is released to open ring engagers 600a'–b' and deploy expandable rings 310a–b. Attachment actuation device 600' is an example of attachment actuation means for approximating one ring to the other ring. Latches 608a'–b' are examples of means for locking the ring engagers against the rings.

Figure 7A:
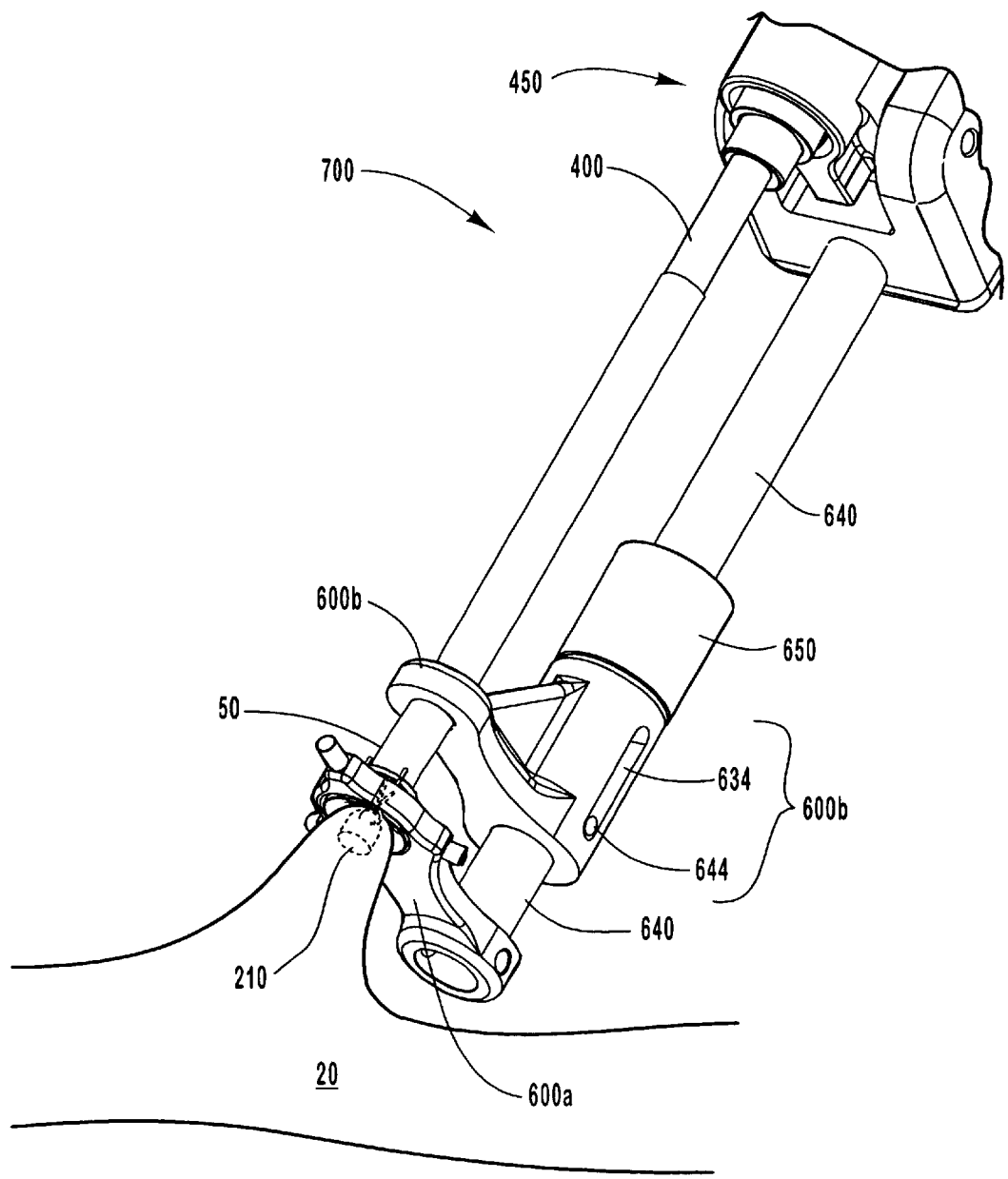
FIG. 7A is a perspective view of the external anastomosis operator cooperating with the anvil depicted in phantom lines to form an anastomosis.
Figure 7B:
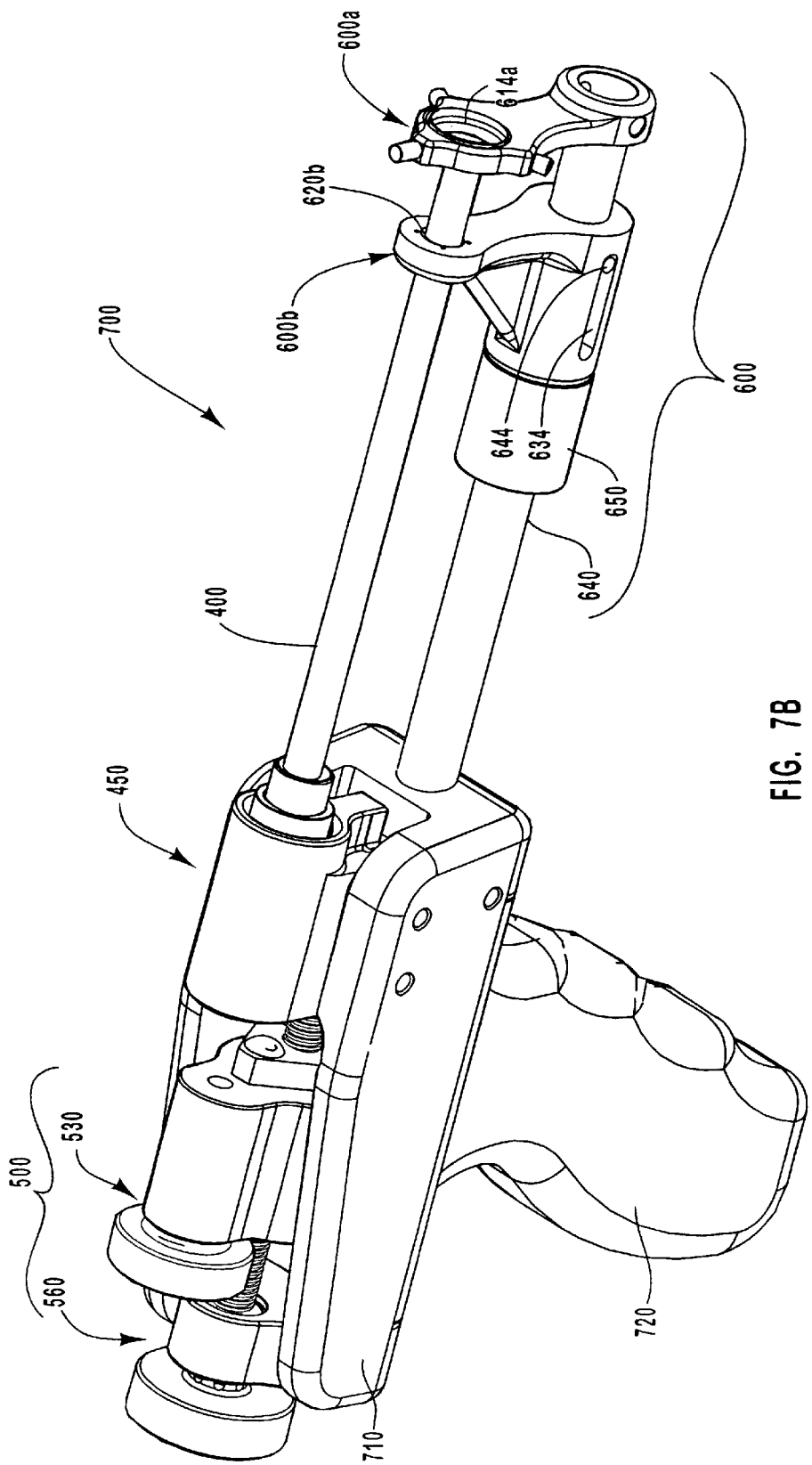
FIG. 7B is a perspective view of an external anastomosis operator.

FIG. 7A shows external anastomosis operator 700 with an attachment actuator 600 engaging an anvil in preparation for cutting an opening in the target vessel. As shown in FIGS. 7A–7B, external anastomosis operator 700 has a body 710 with an optional handle 720. Attached to body 710 are the main components of operator 700. These main components are cutter 400, spring biasing device 450, an anvil pull engager 500 which includes an anvil pull holder 530 and an anvil pull advancer 560, and an attachment actuator 600. Attachment actuator 600 is an additional example of attachment actuation means for approximating one of the rings to the other ring.

The attachment actuation devices and the attachment actuator 600 of external operator 700 may be adapted to enable the orientation of the rings relative to each other to remain essentially the same as the rings are brought together to an anastomosis position. This ability may be necessary for embodiments of the anastomosis device such as device 300' that has no guides. Note that once the opposing ring engagers of the attachment actuation devices or the attachment actuator 600 of external operator 700 have have engaged the rings of an anstomosis device, preferably in a locked configuration, then the rings are easily brought together while maintaining their relative orientation. Note that the opposing ring engagers may be guided together in different ways as shown by the various embodiments. For example, attachment actuation device 600" relies on guides 640" to bring first ring engager 600a" and second ring engager 600b" together. The hinge of attachment actuation device 600' guides the opposing ring engagers 600a'–b' together. As discussed below in reference to attachment actuator 600, rail 640 guides the movement of ring engager to the other. Mechanims adapted to lock the ring engagers against the rings are also discussed below in reference to attachment actuator 600 that function much like latches 608a'–b' discussed above in reference to attachment actuation device 600'.

FIG. 7B provides a perspective view of an external anastomosis operator 700 with its main components identified including: cutter 400, spring biasing device 450, an anvil pull engager 500 which includes an anvil pull holder 530 and an anvil pull advancer 560, and an attachment actuation device 600. Spring biasing device 450 is used to apply pressure against the distal end 418 of cutter 400. One advantage derived form the use of a device such as external anastomosis operator 700 is that such devices have a series of actuators, and by manipulating these actuators the operator can effectuate the different operations at the anastomosis site without actually having to manually and directly operate each element itself.

Figure 7C:
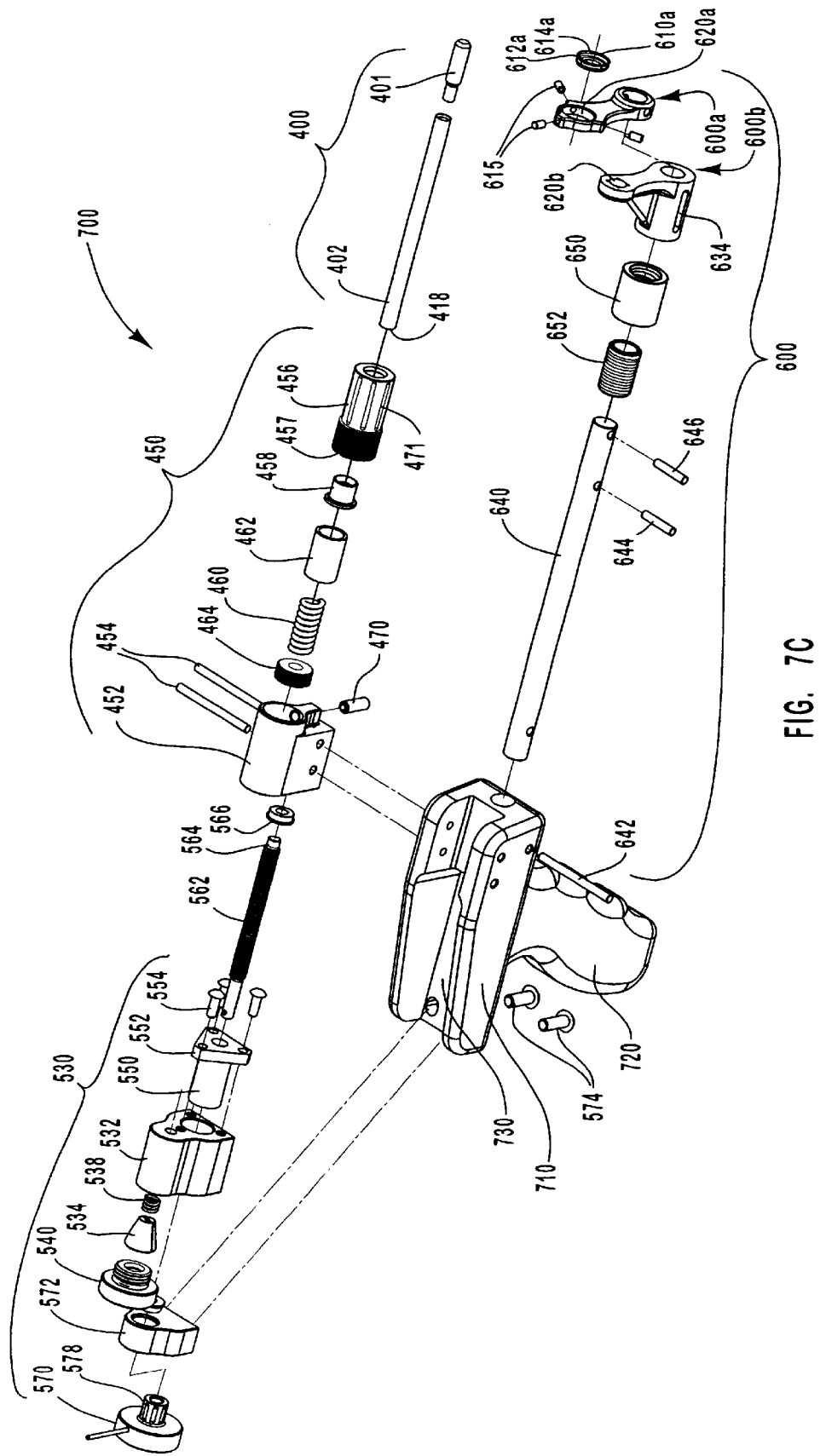
FIG. 7C is an exploded perspective view of the external anastomosis operator.
Figures 7D, 7E:
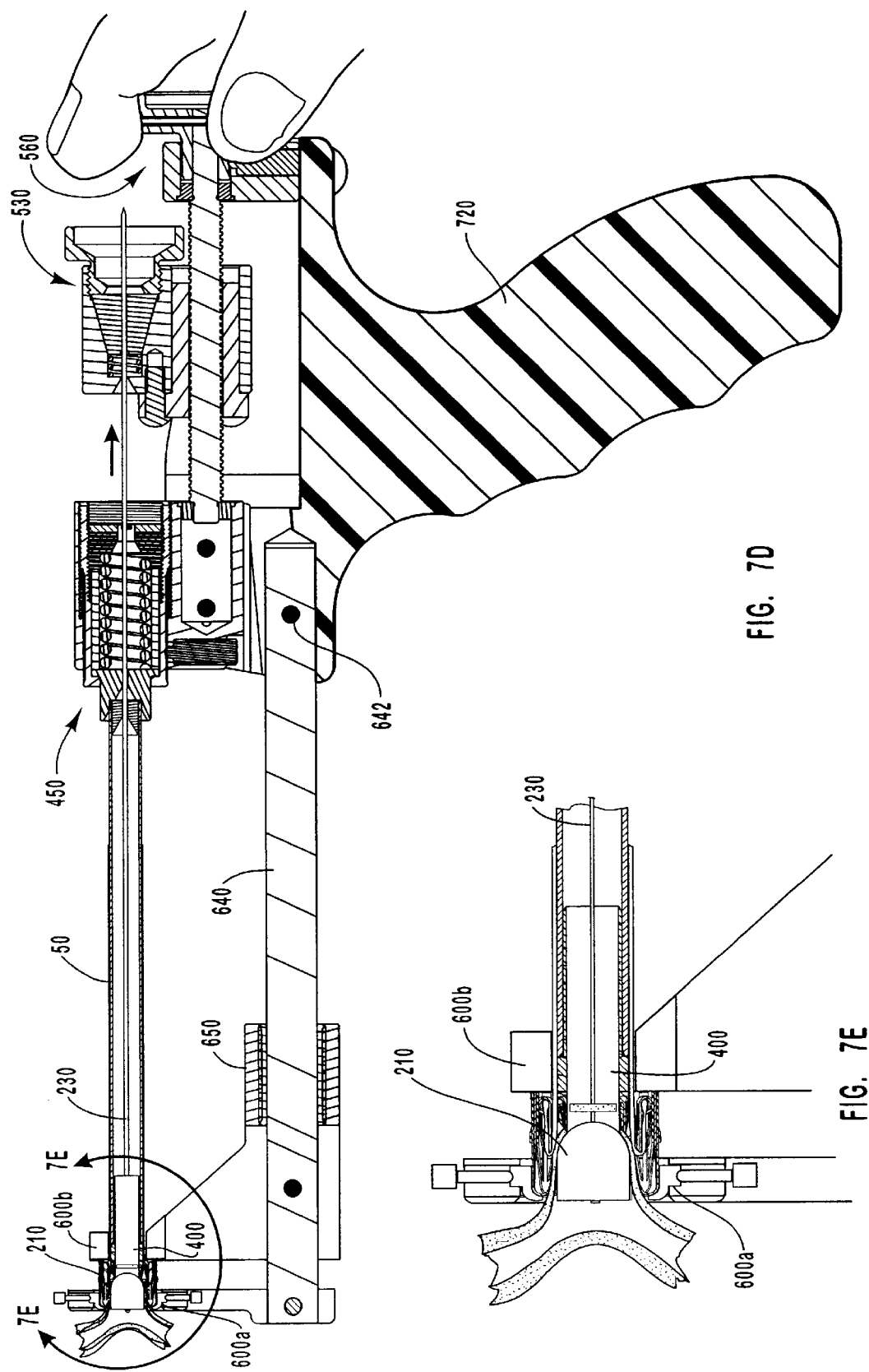
FIG. 7D is a cross-sectional view of the external anastomosis operator.
FIG. 7E is a cross-sectional view of the external anastomosis operator as the anvil pull advancer knob is rotated to pull the anvil pull so that the anvil causes distension of the target vessel into the compression plate apparatus.

FIG. 7C provides an exploded perspective view of all of the components of external anastomosis operator 700 so it is with reference primarily to this view that the details of operator 700 are understood. FIGS. 7D–7E provide cross-sectional views of operator 700 depicting the steps for using operator 700.

Cutter 400 is shown in FIG. 7C as including a tip portion 401 and an extension portion 402. A spring biasing device 450 applies pressure against the distal end 418 of cutter 400. Spring biasing device 450 has a spring mount 452 that is mounted to body 710 via spring mount pins 454. A rotatable spring housing 456 is threadably engaged by spring mount 452. Loaded into rotatable spring housing 456 is a cutter cup 458 that is configured to hold distal end 418 of cutter. Cutter cup 458 has a flange that is pushed against a flange at the proximal end of rotatable spring housing 456 such that cutter cup 458 is held in the proximal end of spring housing 456. A spring 460 is positioned within a spring sleeve 462. Spring 460 and spring sleeve 462 have ends that abut cutter cup 458 and opposite ends that abut threaded jam screw 464. Threaded jam screw 464 is accessible via the distal end of spring mount 452 so that it may be rotated to increase or decrease the tension of spring 460 against cutter cup 458.

Cutter cup 458 moves within rotatable spring housing 456 against spring 460. The pressure of spring 460 against cutter cup 458 enables cutter 400 to apply pressure against anvil 210 as anvil 210 is pulled against cutter 400. This makes it easier to cut the vessels as force is being applied in both directions. It also enables cutter 400 to be pushed back by anvil 210 to allow anvil 210 to further distend the wall of vessel 20 as shown in FIGS. 5A–5B until sufficient pressure is applied by spring 460 to bias cutter 400 forward and by the advancement of anvil 210 by anvil pull 230 to cut the vessel. The gradual increase in pressure also serves to assist a spherical engaging end 212 of anvil 210 to self center on cutter 400. More particularly, anvil 210 may be initially misaligned such that the center of engaging end from which anvil pull extends is positioned on the cutting edge of the cutter. A rapid application of pressure would lock such a misalignment while a gradual increase enables the curvature of spherical engaging end to guide the anvil into a centered orientation.

Another function of spring biasing device is to set the position of cutter 400. Rotatable spring housing 456 has a notch 457 at its distal end that enables a screw driver to rotate rotatable spring housing 456 within spring mount 452 to advance or retract rotatable spring housing 456 within spring mount 452. Movement of rotatable spring housing 456 also moves cutter cup 458, thereby determining the location of distal end 418 of cutter 400 within operator 700. Of course advancement of cutter cup 458 towards the proximal end of operator 700 causes cutting knife 400 to engage anvil 210 closer to first ring 310a while retraction of cutter cup 458 towards the distal end of operator 700 causes cutting knife and anvil to engage each other closer to second ring 310b. The position of cutter 400 is preferably set to enable vessel 20 to be distended in a manner that is optimal for then subsequently everting the portion defining the newly formed opening onto holding surfaces 314a. To carefully identify the length that rotatable spring housing 456 is advanced or retracted, a detent 470 is threaded into spring mount such that it can contact rotatable spring housing and engage the grooves 471 of rotatable spring housing in a manner that enables detent 470 to click as each groove is rotated past detent 470.

Obviously spring biasing device 450 has many variables that impact the manner in which cutter 400 is used in combination with external anastomosis operator 700. Some of these variables include the inherent tension of spring 460, the tension of spring 460 as caused by the position of threaded jam screw 464 in spring mount 452 against spring 460, and the position of the surface which distal end 418 of cutter 400 abuts, namely cutter cup 660 as determined by the position of rotatable spring housing 456 within spring mount 452.

Spring biasing device 450 is an example of spring biasing means for providing tension against the cutting means as the cutting means engages the anvil means of the intraluminally directed anvil apparatus. The spring biasing means provides an amount of tension that enables the cutting means to form the first vessel opening after the wall of the first vessel has been distended by the action of the anvil means being pulled into the openings of the ring assembly such that forming the first vessel opening results in at least partial eversion of the portion of the first vessel defining the first vessel opening.

As indicated above, anvil pull engager 500 has two primary components including an anvil pull holder 530 and anvil pull advancer. Anvil pull holder 530 receives anvil pull 230 via spring biasing device 450. More particularly, anvil pull 230 extends through cutter cup 458, rotatable spring housing 456, spring 460 and sleeve 462 around spring 460, and out of threaded jam screw 464.

Anvil pull holder 530 includes a holder mount 532 positioned in track 730 of body 710. In this embodiment, holder mount is moveable so that the anvil pull can be advanced after it is held. However, in other embodiments, the anvil pull holder may just lock the anvil pull into position such that the cutter is moved against a stationary anvil. Similarly, the spring biasing device 450 may be eliminated so that the vessel is cut only by pressure exerted by the anvil pull against the cutter. As discussed above, while the cutter and the anvil may engage each other in these arrangements, it is preferable for the cutter to apply some pressure as the anvil pull is advanced against the cutter.

Holder mount 532 may be utilized in different ways to hold anvil pull 230. Holder 530 has a split cone 534 inserted into a tapered chamber 536 against a spring 538. Anvil pull 230 extends through apertures in holder mount 532, spring 538, split cone 534 and out of an aperture centered in holder knob 540. Holder knob 540 is threadably engaged by holder mount 532 such that rotation of holder knob 540 advances split cone 534 in tapered chamber 536 causing split cone to lock onto anvil pull 230. Holder mount is slotted at its distal end as is holder knob. By aligning slot 542 of holder knob 540 with the insert slot 544 of holder mount, anvil pull 230 can be bent so that it extends through both holder knob slot 542 and insert slot 544. Then holder knob 540 can then be rotated so that the bent portion of anvil pull 230 is rotated into one of the locking slots 546a–b that extend perpendicularly from insert slot 544. This securely locks anvil pull into position. Anvil pull 230 can be locked through the use of slots instead of or in addition to the use of split cone 534 in tapered chamber 536.

Since anvil pull holder 530 is moveable it threadably engages rotatable lead screw 562 of anvil pull advancer. More particularly, lead screw 562 is threadably engaged by anti-backlash nut 550 which is fixedly attached to holder mount 532. Anti-backlash nut 550 has an attachment face 552 through which a plurality of attachment face screws 554 extend to hold holder mount 532 and anti-backlash nut 550 together.

Lead screw 562 has a proximal pivot end 564 that rotates within a bushing 566 positioned within a recess in spring mount 452. Lead screw also has a distal pivot end 568 that is attached to advancer knob 570 to rotate lead screw 562. Advancer knob 570 rotates within an advancer knob mount 572 which is attached to body 710 in groove 730 via advancer knob mount bolts 574. As shown in FIG. 7D, distal pivot end 568 rotates in a bushing 576 positioned within an aperture of advancer knob mount 572.

Advancer knob 570 has a stem with a plurality of grooves 578 that engage a detent 580 to click so that the incremental rotation of advancer knob 570 can be carefully counted to determine the length that the anvil is moved in the anastomosis device as the anvil pull is advanced. As shown in FIG. 7C, detent 580 is threaded into advancer knob mount 572 such that it can contact grooves 578 in the stem of advancer knob 570 to click as each groove is rotated past detent 580.

FIG. 7E depicts advancer knob 570 being rotated to move anvil pull advancer 560 so that it can urge anvil pull 230 in a manner such that anvil 210 is advanced within anastomosis device 300. As advancer knob 570 is rotated, lead screw 562 is thereby rotated. Since anvil pull holder 530 is threadably engaged on rotatable lead screw 562 and is locked in track 730, anvil pull holder 530 can only move forward and backward as lead screw 562 is rotated.

FIG. 7F depicts attachment actuation device 600 being engaged. Attachment actuation device 600 has a first ring engager 600a and a second ring engager 600b. First ring engager 600a and a second ring engager 600b each respectively utilize an optional adaptor 610a–b to engage first and second rings 310a–b. First ring engager 600a and second ring engager 600b each have a cutter aperture 620a and 620b. Cutter 400 extends through these aligned apertures 620a–b. First ring engager 600a is positioned on rail 640 such that it extends slightly beyond cutting edge 414 of cutter 400. This difference in length enables first ring 300a to be held slightly beyond cutter in a manner that permits the wall of vessel 20 to be pulled into anastomosis device as shown in FIGS. 7D–7F and distended as needed.

Rail 640 is attached to body 710 via rail pin 642. A groove pin 644 extends through rail 640. A first ring holder 646 holds first ring engager 600a on the proximal end of rail 640.

First ring engager 600a is fixedly mounted on rail 640 via pin 646 while second ring engager 600b is movably mounted on rail 640. Second ring engager 600b has a groove 634 through which groove pin 644 extends. The configuration of groove pin 644 in groove 634 enables second ring engager 600b to be held in a fixed orientation such that it can be moved back and forth as needed with respect to first ring engager 600a.

Second ring engager is moved on rail 640 by rotating threaded compressor sleeve 650 which engages a threaded rail sleeve 648. Threaded rail sleeve 648 may be adhered onto rail 640 or be an integral component. Rail 640 and its threaded rail sleeve 648 or threaded rail portion combined with compressor sleeve 650 are means for advancing one ring engager towards the other ring engager.

Set screws 615 lock first ring engager 600a on first ring 310a. Second ring engager 600b has a latch (not shown) that enables engager 600b to lock onto second ring 310b. Once the anastomosis is complete, set screws 615 and the latch are released to release the first and second ring engagers from the expandable rings. Note that there are many other ways for locking the rings with first and second ring engager 600a–b such as the use of conventional quick release configurations. Quick release configurations, latches and set screws are all examples of means for locking the ring engagers against the rings.

The paired expandable anastomosis device of the present invention is preferably used for vascular anastomosis, however, the present invention is not limited to such use. Nor is the anastomosis device limited to use with any particularly sized vessel. For example, vessels may be joined with diameters ranging from about 2 mm to about 20 mm, but there is no fundamental limitation for using embodiments of this invention with graft vessels with diameters less than 2 mm.

It will be obvious to those having skill in the art that many changes may be made to the details of the above-described embodiments of this invention without departing from the underlying principles thereof. The scope of the present invention should, therefore, be determined only by the following claims.

What is claimed is:

1. A paired anastomosis device for holding a first vessel together with a second vessel comprising:
   first ring means for providing support for a first vessel at a first vessel opening, wherein the first ring means has a first ring opening,
   second ring means for providing support for a second vessel at a second vessel opening, wherein the second ring means has a second ring opening,
      wherein each ring means is adapted to expand and contract to enable each respective vessel opening to change in diameter, and
      wherein the ring means are configured to be structurally linked in a manner such that the first and second ring means expand and contract in unison and such that the first vessel remains anastomosed to the second vessel at the first and second vessel openings as the first and second ring means expand and contract.

2. The anastomosis device of claim 1, further comprising locking means for locking the first ring means and the second ring means together such that the first vessel and the second vessel remain anastomosed together.

3. The anastomosis device of claim 2, wherein the locking means comprises guide means for guiding the movement of one ring means relative to the other ring means from a loading position with the first ring means offset from the second ring means to an anastomosis position.

4. The anastomosis device of claim 2, wherein the first and second ring means are adapted to cooperate with attachment actuation means for approximating one of the ring means to the other ring means such that the device is moved from a loading position to an anastomosis position.

5. The anastomosis device of claim 1, wherein the first ring means further comprises holding means for holding the first vessel at the first vessel opening, and
   wherein the second ring means further comprises holding means for holding the second vessel at the second vessel opening.

6. The anastomosis device of claim 5, wherein the holding means of at least one of the rings means has anchor means for more securely anchoring a vessel on the holding means.

7. A paired anastomosis device for holding a first vessel together with a second vessel comprising:
   a first ring having holding surfaces that define a first ring opening, wherein the holding surfaces are adapted to hold a portion of a first vessel defining a first vessel opening such that the first vessel opening is at the first ring opening,
   a second ring having a plurality of holding surfaces that define a second ring opening, wherein the holding surfaces are adapted to hold a portion of a second vessel defining a second vessel opening such that the second vessel opening is at the second ring opening,
      wherein each ring is adapted to expand and contract to enable each respective vessel opening to change in diameter, and
      wherein the rings are configured to be structurally linked in a manner such that the first and second rings expand and contract in unison and such that the first vessel remains anastomosed to the second vessel at the first and second vessel openings as the first and second rings expand and contract.

8. The anastomosis device of claim 7, further comprising a plurality of guideposts extending from one of the rings and a plurality of guides fixedly connected to the other ring, wherein the guideposts are positioned to slide into the guides in order to guide the rings from a loading position to an anastomosis position.

9. The anastomosis device of claim 8, wherein the guides are sized to frictionally engage the guideposts such that the rings are maintained in the anastomosis position after the rings are brought together.

10. The anastomosis device of claim 7, wherein one of the rings has a plurality of legs with locking extensions and the opposite ring has a plurality of legs with slots positioned to receive the locking extensions, such that the rings are maintained in the anastomosis position after the rings are brought together.

11. The anastomosis device of claim 7, wherein each vessel has an intimal layer, and
   wherein the holding surfaces of each ring are positioned to capture vessel tissue in an everted configuration so that when the rings are in an anastomosis position the intimal layer of the portion of the first vessel defining a first vessel opening contacts the inimal layer of the portion of the second vessel defining a second vessel opening.

12. The paired anastomosis device of claim 7, wherein each vessel has an adventitial layer,
   wherein the holding surfaces of the first ring contact the adventital surfaces of the portion of the first vessel defining a first vessel opening, and
   wherein the holding surfaces of the second ring contact the adventital surfaces of the portion of the second vessel defining a second vessel opening.

13. The anastomosis device of claim 7, wherein each ring comprises a plurality of flexible segments.

14. The anastomosis device of claim 13, wherein each flexible segment comprises two adjoining arms in a V-shaped configuration.

15. The anastomosis device of claim 13, wherein each flexible segment has a configuration that is selected from the group consisting of a U-shaped configuration, a quadrilateral shaped configuration, a circular configuration, an elliptical configuration, a spiral-shaped configuration, and an oval-shaped configuration.

16. The anastomosis device of claim 13, wherein the holding surfaces of each ring are holding tabs.

17. The anastomosis device of claim 16, wherein each flexible segment of the plurality of flexible segments of each ring is adjoined to an adjacent flexible segment by a connecting joint, wherein each flexible segment of each ring has a flexible segment joint, wherein the holding tabs of the first ring extend from the connecting joints, wherein the holding tabs of the second ring extend from the flexible segment joints.

18. A paired anastomosis device for holding a first vessel together with a second vessel comprising:
   first ring means for providing support for a first vessel at a first vessel opening, wherein the first ring means has a first ring opening,
   second ring means for providing support for a second vessel at a second vessel opening, wherein the second ring means has a second ring opening,
      wherein each ring means is adapted to be in a compressed position as the first vessel and second vessel are anastomosed together such that each respective ring opening and respective vessel opening have an initial diameter, and
      wherein at least one ring means is adapted to radially expand to a deployed position after the first vessel and second vessel are anastomosed together such that each ring means and vessel opening has a greater diameter than the initial diameter of each respective ring means and vessel opening.

19. A paired anastomosis device for holding a first vessel together with a second vessel comprising:
   a first ring having holding surfaces that define a first ring opening, wherein the holding surfaces are adapted to hold a portion of a first vessel defining a first vessel opening such that the first vessel opening is at the first ring opening,
   a second ring having a plurality of holding surfaces that define a second ring opening, wherein the holding surfaces are adapted to hold a portion of a second vessel defining a second vessel opening such that the second vessel opening is at the second ring opening,
      wherein each ring is adapted to be in a compressed position as the first vessel and second vessel are anastomosed together such that each respective ring opening and respective vessel opening have an initial diameter, and
      wherein at least one ring is adapted to radially expand to a deployed position after the first vessel and second vessel are anastomosed together such that each ring and vessel opening has a greater diameter than the initial diameter of each respective ring and vessel opening.

20. A paired anastomosis device for holding a first vessel together with a second vessel comprising:

a first ring having a plurality of holding surfaces that define a first ring opening, wherein the holding surfaces are adapted to hold a portion of a first vessel defining a first vessel opening such that the first vessel opening is at the first ring opening, a second ring having a plurality of holding surfaces that define a second ring opening, wherein the holding surfaces are adapted to hold a portion of a second vessel defining a second vessel opening such that the second vessel opening is at the second ring opening, wherein each ring has a plurality of flexible segments from which the respective holding surfaces extend, and guides positioned to provide guided coaxial movement of the rings relative to each other so that the rings can be moved from a loaded position with the first ring offset from the second ring to an anastomosis position with the first vessel is anastomosed to the second vessel at the first and second vessel openings, wherein the plurality of flexible segments of each ring are adapted to enable each respective ring opening and respective vessel opening to change in diameter as each ring expands and contracts in response to changes in fluid pressure.

21. A method for holding a first vessel together with a second vessel comprising:

holding a portion of a first vessel defining a first vessel opening on a first ring, wherein the first ring is configured such that the diameter of a first ring opening defined by the first ring can expand and contract;

holding a portion of a second vessel defining a second vessel opening on a second ring, wherein the second ring is configured such that the diameter of a second ring opening defined by the second ring can expand and contract;

bringing the first and second rings together such that the first vessel is in fluid communication with the second vessel.

22. The method of claim 21, further comprising the step of locking the first ring together with the second ring such that the first vessel and the second vessel remain anastomosed together.

23. The method of claim 21, wherein the first ring has one or more holding surfaces for holding the portion of the first vessel defining the first vessel opening, and wherein the second ring has one or more holding surfaces for holding the portion of the second vessel defining the second vessel opening.

24. The method of claim 23, wherein the holding surfaces are holding tabs.

25. The method of claim 23, wherein one or more of the holding surfaces have anchor means for more securely anchoring the vessels onto the holding surfaces.

26. The method of claim 21, wherein the first ring has a plurality of guideposts extending therefrom and the second ring has a plurality of guides, and wherein the guideposts are positioned to slide into the guides as the first and second rings are brought together.

27. The method of claim 26, wherein the guides are sized to frictionally engage the guideposts such that the rings are maintained in the anastomosis position after the rings are brought together.

28. The method of claim 21, wherein each ring comprises a plurality of flexible segments.

29. The method of claim 28, wherein each ring has one or more holding tabs.

30. The method of claim 29, wherein each flexible segment is adjoined to an adjacent flexible segment by a connecting joint, wherein each flexible segment has a flexible segment joint, wherein the holding tabs of the first ring extend from the connecting joints, and wherein the holding tabs of the second ring extend from the flexible segment joints.

31. The method of claim 28, wherein each flexible segment comprises two adjoining arms in a V-shaped configuration.

32. The method of claim 28, wherein each flexible segment has a configuration that is selected from the group consisting of a U-shaped configuration, a quadrilateral-shaped configuration, a circular configuration, an elliptical configuration, a spiral-shaped configuration, and an oval-shaped configuration.

33. The method of claim 21, wherein after the first and second rings are brought together, the first and second rings expand and contract in unison such that the first vessel remains anastomosed to the second vessel as the first and second rings expand and contract.

34. The method of claim 21, wherein the step of bringing the first and second rings together is achieved by using an attachment actuation device, which the first and second rings are adapted to cooperate with.

35. The method of claim 21, wherein the step of holding the first vessel is achieved after everting the portion of the first vessel defining the first vessel opening.

36. The method of claim 21, wherein the steps of holding the first and second vessels are both achieved by everting the portion of the first vessel defining the first vessel opening over the first ring and everting the portion of the second vessel defining the second vessel opening over the second ring.

* * * * *